(12) United States Patent
Tanghoj et al.

(10) Patent No.: US 7,094,220 B2
(45) Date of Patent: Aug. 22, 2006

(54) CATHETER ASSEMBLY INCLUDING A CATHETER APPLICATOR

(75) Inventors: Allan Tanghoj, Kokkedal (DK); Lars Bogelund Jensen, Rødovre (DK)

(73) Assignee: Coloplast A/S, Humlebaek (DK)

( * ) Notice: Subject to any disclaimer, the term of this patent is extended or adjusted under 35 U.S.C. 154(b) by 331 days.

(21) Appl. No.: 10/183,984

(22) Filed: Jun. 28, 2002

(65) Prior Publication Data

US 2003/0018322 A1    Jan. 23, 2003

Related U.S. Application Data

(63) Continuation-in-part of application No. 10/026,819, filed on Dec. 27, 2001, and a continuation-in-part of application No. 09/893,514, filed on Jun. 29, 2001, now abandoned.

(30) Foreign Application Priority Data

| Jun. 29, 2001 | (DK) | ................................ 2001 01041 |
| Sep. 24, 2001 | (DK) | ................................ 2001 01386 |
| Dec. 13, 2001 | (DK) | ................................ 2001 01869 |
| Dec. 13, 2001 | (DK) | ................................ 2001 01870 |
| Apr. 17, 2002 | (DK) | ................................ 2002 00569 |
| Apr. 17, 2002 | (DK) | ................................ 2002 00570 |
| Jun. 13, 2002 | (DK) | ................................ 2002 00895 |

(51) Int. Cl.
*A61M 5/32* (2006.01)
*A61M 25/01* (2006.01)
*A61F 11/00* (2006.01)

(52) U.S. Cl. ...................... 604/177; 604/178; 604/250; 604/528; 606/108

(58) Field of Classification Search ................ 604/540, 604/34, 533, 537, 159, 164.13, 165.03, 177, 604/178, 528, 32, 171, 250; 251/4–10; 606/108
See application file for complete search history.

(56) References Cited

U.S. PATENT DOCUMENTS

| 3,186,410 | A | | 6/1965 | Buono ......................... 128/275 |
| 3,537,451 | A | * | 11/1970 | Beck et al. ............. 604/165.03 |
| 3,661,153 | A | | 5/1972 | Polk et al. .................... 128/275 |
| 3,769,981 | A | | 11/1973 | McWhorter |
| 3,853,130 | A | | 12/1974 | Sheridan .................. 128/349 R |
| 3,854,483 | A | | 12/1974 | Powers .................... 128/349 R |
| 3,865,666 | A | | 2/1975 | Shoney |
| 3,867,945 | A | | 2/1975 | Long |
| 3,894,540 | A | | 7/1975 | Bonner, Jr. .............. 128/349 R |
| 4,041,122 | A | | 8/1977 | Quick et al. |
| 4,188,954 | A | | 2/1980 | Patel et al. |
| 4,246,909 | A | | 1/1981 | Wu et al. |

(Continued)

FOREIGN PATENT DOCUMENTS

CN       2168601 Y       6/1994

(Continued)

*Primary Examiner*—Tatyana Zalukaeva
*Assistant Examiner*—Michael G. Bogart
(74) *Attorney, Agent, or Firm*—Jacobson Holman PLLC

(57) ABSTRACT

The present invention is a catheter assembly allowing for non-contaminated insertion of a catheter into a urinary canal. The assembly includes a package for the catheter and an applicator to be used for guiding the catheter into the urinary canal without touching the catheter by holding the catheter via walls of the applicator. The assembly further comprises clamping means for pressing the walls of the applicator into engagement with the catheter. The present invention further relates to an applicator with integrated clamping means to be used with the assembly.

15 Claims, 29 Drawing Sheets

U.S. PATENT DOCUMENTS

| | | | |
|---|---|---|---|
| 4,284,459 A | 8/1981 | Patel et al. | |
| 4,363,406 A | 12/1982 | Salvadori | 206/604 |
| 4,421,509 A | 12/1983 | Schneider et al. | 604/317 |
| 4,511,358 A | 4/1985 | Johnson et al. | |
| 4,588,160 A * | 5/1986 | Flynn et al. | 251/10 |
| 4,615,472 A | 10/1986 | Nash | 226/127 |
| 4,673,161 A * | 6/1987 | Flynn et al. | 251/10 |
| 4,743,236 A | 5/1988 | Manschot | |
| 4,802,650 A | 2/1989 | Stricker | 251/117 |
| 4,850,350 A | 7/1989 | Jackson | |
| 5,035,399 A * | 7/1991 | Rantanen-Lee | 251/10 |
| 5,147,341 A | 9/1992 | Starke et al. | 604/349 |
| RE34,223 E * | 4/1993 | Bonaldo | 604/192 |
| 5,242,398 A | 9/1993 | Knoll et al. | 604/101 |
| 5,320,613 A | 6/1994 | Houge et al. | 604/283 |
| 5,354,263 A | 10/1994 | Coll | |
| 5,391,155 A | 2/1995 | Sachse | |
| 5,409,469 A | 4/1995 | Schaerf | 604/282 |
| 5,454,798 A | 10/1995 | Kubalak et al. | |
| 5,510,065 A | 4/1996 | McFarlane | |
| 5,643,236 A | 7/1997 | Hadley | |
| 5,690,645 A * | 11/1997 | Van Erp | 606/108 |
| 5,745,926 A | 5/1998 | Cailleteau | 4/144.1 |
| 6,053,905 A * | 4/2000 | Daignault et al. | 604/544 |
| 6,059,107 A | 5/2000 | Nosted et al. | |
| 6,090,075 A * | 7/2000 | House | 604/172 |
| 6,602,244 B1 | 8/2003 | Kavanagh et al. | |
| 2002/0103467 A1* | 8/2002 | Kubalak | 604/327 |
| 2003/0018293 A1 | 1/2003 | Tanghoj et al. | |
| 2003/0018322 A1 | 1/2003 | Tanghoj et al. | |
| 2004/0153051 A1 | 8/2004 | Israelsson et al. | |
| 2004/0158231 A1 | 8/2004 | Tanghoj et al. | |
| 2004/0163980 A1 | 8/2004 | Tanghoj et al. | |
| 2004/0236293 A1 | 11/2004 | Tanghoj et al. | |
| 2004/0254562 A1 | 12/2004 | Tanghoj et al. | |

FOREIGN PATENT DOCUMENTS

| | | |
|---|---|---|
| DE | 24 62 537 | 6/1977 |
| DE | 28 01 851 | 7/1978 |
| DE | 3816906 | 11/1989 |
| DE | 4140099 | 5/1993 |
| DE | 198 26 746 | 11/1999 |
| DE | 201 03 653 | 6/2001 |
| DK | 172941 | 10/1999 |
| DK | 173714 | 7/2001 |
| EP | 0 206 558 A1 * | 12/1986 |
| EP | 0336984 | 12/1990 |
| EP | 0 570 370 | 11/1993 |
| EP | 0 658 488 | 6/1995 |
| EP | 0 807 447 | 11/1997 |
| EP | 0824930 | 2/1998 |
| EP | 0925802 | 6/1999 |
| EP | 1 023 882 | 8/2000 |
| EP | 0923398 | 11/2001 |
| EP | 0959930 | 12/2002 |
| EP | 0923390 | 4/2003 |
| FR | 2293948 | 7/1976 |
| GB | 1 482 873 | 8/1977 |
| GB | 1493257 | 11/1977 |
| GB | 1 598 843 | 9/1981 |
| GB | 2 193 485 | 2/1988 |
| GB | 2230702 | 10/1990 |
| GB | 2231801 | 11/1990 |
| GB | 2 278 285 | 11/1994 |
| GB | 2 336 830 | 11/1999 |
| HU | 187 406 | 12/1987 |
| HU | 189 812 | 8/1988 |
| HU | 263 A | 4/1994 |
| HU | 210 728 B | 7/1995 |
| HU | 213 805 B | 10/1997 |
| HU | 215 792 B | 3/1999 |
| HU | P9903763 | 3/2000 |
| HU | 217 867 B | 4/2000 |
| HU | 219 423 B | 4/2001 |
| HU | 219 512 B | 4/2001 |
| HU | 220 326 B | 12/2001 |
| HU | P0201498 | 9/2002 |
| HU | 222 366 B1 | 6/2003 |
| HU | 223 145 B1 | 3/2004 |
| SE | 518 002 | 8/2002 |
| WO | 89/02763 | 4/1989 |
| WO | 90/00960 | 2/1990 |
| WO | WO 91/18640 | 12/1991 |
| WO | 92/07607 | 5/1992 |
| WO | 92/13718 | 8/1992 |
| WO | WO 92/18310 | 10/1992 |
| WO | WO 93/04723 | 3/1993 |
| WO | 93/19717 | 10/1993 |
| WO | WO 94/08653 | 4/1994 |
| WO | WO 95/24235 | 9/1995 |
| WO | 96/19254 | 6/1996 |
| WO | WO 96/19254 | 6/1996 |
| WO | WO 97/07707 | 3/1997 |
| WO | 97/26937 | 7/1997 |
| WO | WO 97/47349 | 12/1997 |
| WO | 98/06642 | 2/1998 |
| WO | 98/11932 | 3/1998 |
| WO | 98/58988 | 12/1998 |
| WO | 98/58989 | 12/1998 |
| WO | 98/58990 | 12/1998 |
| WO | 99/23978 | 5/1999 |
| WO | 99/30761 | 6/1999 |
| WO | 00/16843 | 3/2000 |
| WO | WO 00/16843 | 3/2000 |
| WO | 00/30575 | 6/2000 |

\* cited by examiner

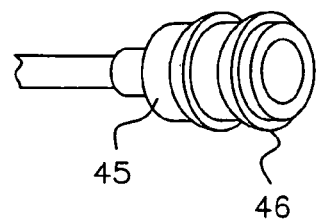
FIG. 4a
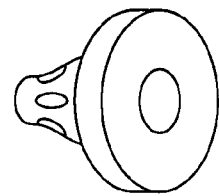
FIG. 4b
FIG. 4c
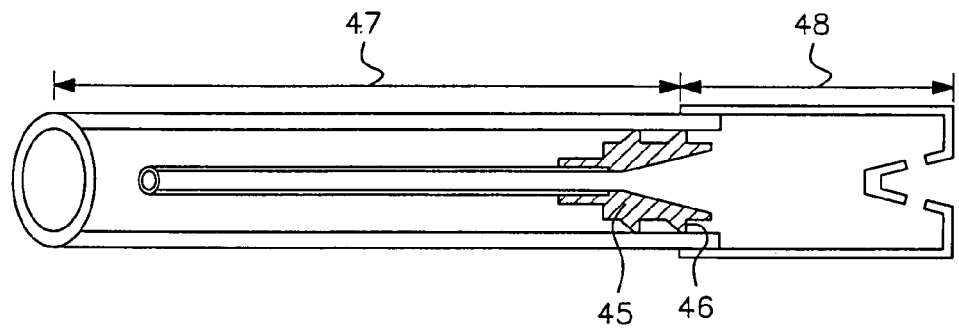
FIG. 4d
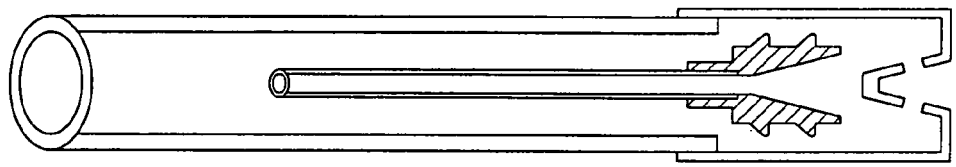
FIG. 4e
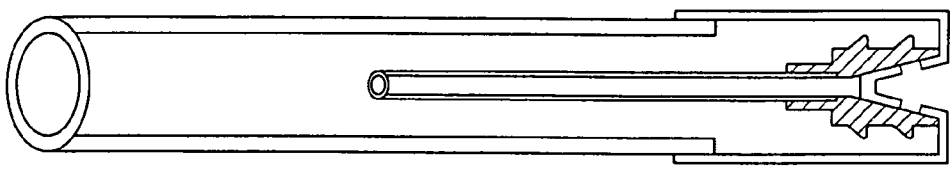

FIG. 29a
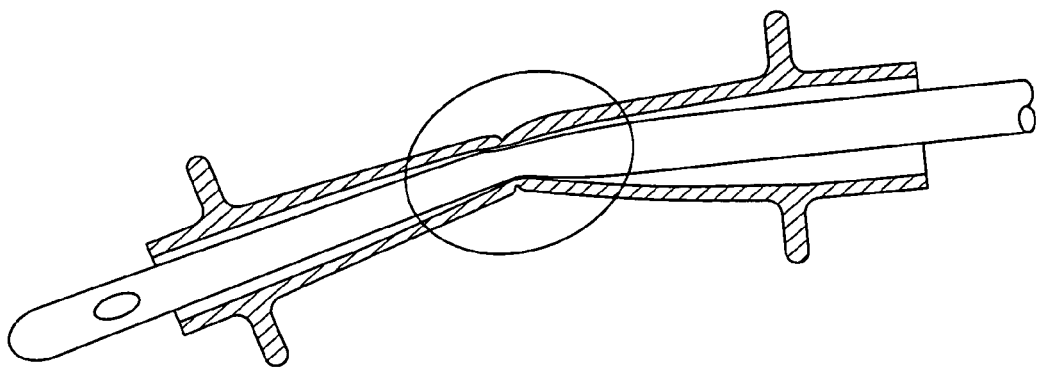
FIG. 29b    FIG. 29c    FIG. 29d
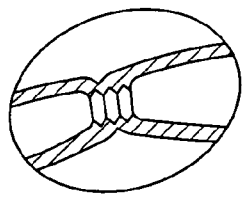 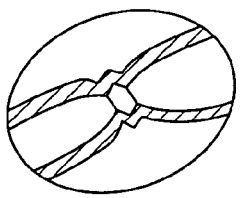 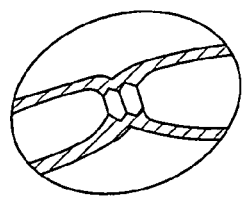
FIG. 29e    FIG. 29f    FIG. 29g
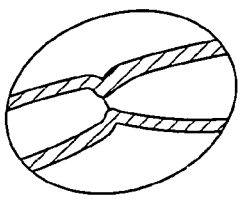 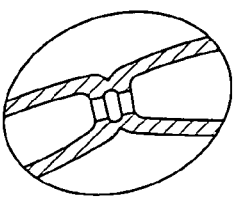 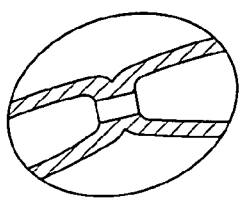

CATHETER ASSEMBLY INCLUDING A CATHETER APPLICATOR

This is a Continuation-in-Part of U.S. Ser. No. 09/893,514 filed Jun. 29, 2001, now abandoned, and a Continuation-in-Part of U.S. Ser. No. 10/026,819, filed on Dec. 27, 2001, which applications are hereby incorporated by reference.

FIELD OF THE INVENTION

The present invention relates to a urinary catheter assembly comprising a package allowing for storage of the catheter and for contamination free insertion of the catheter into a natural or an artificial urinary canal of an individual.

BACKGROUND OF THE INVENTION

Catheters for draining the bladder are increasingly used for intermittent as well as indwelling or permanent catheterisation. Typically, catheters are used by patients suffering from urinary incontinence or by disabled individuals like para- or tetraplegics who may have no control permitting voluntary urination and for whom catheterisation may be the way of urinating.

Typically, catheters are provided to the user enveloped in a completely sealed and sterilised package. During use and prior to insertion, the catheter is removed completely from the package whereby a potential contamination of the catheter may occur, e.g. if the user unintentionally touches the catheter or if the catheter touches surrounding obstacles such as a toilet seat or a wash basin etc. Catheter packages and assemblies of catheters and packages exist, wherein both a proximal end and a distal end of the package may be opened thus allowing for draining the urine through a catheter which is still at least partly enveloped in the package. Thereby, the user may urinate without completely exposing the catheter and the risk of contamination is therefore reduced. There is however still a severe risk that the handling of the catheter may cause an unwanted contamination, not least if the user touches the catheter during the insertion thereof.

WO 00/30575 discloses a urinary catheter assembly comprising a case and an applicator for non-contaminating insertion of a urinary catheter into a urinary canal. The disclosed applicator comprises a compartment with a soft resilient wall adapted to be squeezed into engagement with the catheter in question. The applicator thus reduces the risk of contaminating the catheter by allowing the user to insert the catheter without touching it by hand. The use of the disclosed compartment requires not only dexterity but also certain strength for the user to squeeze the compartment sufficiently tight against the outer surface of the catheter to allow manipulation thereof. The manipulation of the catheter through the compartment wall is even more difficult when the catheter is coated with a friction reducing substance.

DESCRIPTION OF THE INVENTION

It is an object of the present invention to overcome the above described disadvantages of the known catheter assemblies by providing a catheter assembly which, according to a first aspect of the invention, allows for non contaminated insertion of a catheter into a urinary canal, said assembly comprising:

- a catheter defining a conduit between a proximal end adapted for insertion into a body opening of an individual and an opposite distal end,
- a package having a hose with a cavity for accommodation of the catheter and, in a proximal end of the package, an opening for dispensing the proximal end of the catheter from the package, and
- an applicator comprising:
    - a tubular compartment with a first open end, the compartment being adapted to receive at least a part of a catheter and being formed with a wall having an inner surface facing the catheter and an outer surface, the wall being provided with a flexible zone so as to allow the inner surface of the compartment wall to be squeezed into engagement with the catheter upon a pressure applied to the outer surface of the wall, and
    - clamping means.

The catheter or at least a part of the catheter could be made from silicone or from a thermoplastic elatomeric material, other thermoplastic materials, curable elastomeric materials, polyamide resins or elastomers or any mixture thereof, i.e. the group may comprise materials like, PVC, PU, PE, EVA, latex, and/or Kraton™.

Preferably the catheter is provided with a bending moment defined as the product between E-modulus and moment of inertia of at least 1 MPa*mm$^4$.

Since the proximal (insertable) end of the catheter, for male individuals, must pass prostate in a curved passage, the proximal end portion of the catheter, e.g. the first 10–50 mm. such as 20–40 mm., such as 25–35 mm, such as the first 30 mm. of the catheter may be provided with an even lower bending moment defined as the product between E-modulus and moment of inertia of less than e.g. 0,6 MPa*mm$^4$ or even less than 0,3 MPa*mm$^4$. Other parts of the catheter, e.g. a distal end portion where the urine is drained Into the toilet, a bag or place of disposal, may similarly be provided with a different bending moment. As another alternative, the entire catheter may be made from a soft resilient material, e.g. silicone, with an E-modulus which is different, e.g. lower than the above mentioned. Moreover, in some cases the catheter may be provided with an E-modulus which is higher than the above mentioned. As an example a stiff catheter, e.g. a catheter made of metal may provided.

The cross-sectional flow area or the hydraulic radius defined as the ratio of the cross-sectional flow area to the wetted perimeter, may be selected independently upon the length, e.g. on the basis of the size of the urinary canal, which size preferably differs between the individuals.

Catheters typically have a certain section adapted to be inserted into the urinary canal. This insertable section may be provided over the entire length of the catheter or it may be a certain length of the catheter, either measured from the insertable proximal end of the catheter or from inlet openings typically provided nearby the proximal end of the catheter. The insertable section may for some catheters be defined by a section provided with a frictional reducing surface. The catheter may be provided in a length up to 400 mm. or more and the entire length may be insertable. Since the length of the urinary canal is typically much shorter, the catheter may preferably be provided with an insertable length in the range of 50–90 mm., such as in the range of 55–85 mm., such as in the range of 60–80 mm. such as with a length in the size of 70 mm. which length has been found to be a suitable insertable length for most female individuals. For male individuals, the insertable length of the catheter may preferably be provided in the range of 180–350 mm., such as in the range of 190–310 mm., such as in the range of 210–290 mm. such as in the size of 260 mm. For the male individuals, it may further be preferred to provide at least a part of the inserted end of the catheter in a material or in dimensions so that the tube becomes very flexible in order to easy the passage of the catheter past prostate.

The inner cross-sectional shape of the catheter should preferably be substantially circular with a cross-sectional area in the range of 0,5 mm$^2$–50 mm$^2$.

The outer cross-sectional shape and size of the catheter should match the size of the urinary canal and/or the passage into the bladder. Typical catheter sizes vary between CH6 and CH32.

The catheter or at least a section thereof may be provided with a hydrophilic surface. When treated with a liquid swelling medium, such a surface will provide an excellent lubrication for the insertion and also provide compatibility with the body tissue.

However, the catheter may also be of the traditional type wherein a low friction, character is obtained by application of a lubricant different from water, the lubricant being applied to at least a section of the catheter.

The liquid swelling medium for a hydrophilic surface may be provided in the package, especially in the upper storage compartment, near the proximal end of the catheter, when the catheter is arranged in the package. Thereby, the low friction character will be initiated already when the catheter is being arranged in the package. The liquid swelling medium may simply be a saline solution, a bactericidal solution capable of swelling the hydrophilic surface and capable of keeping the surface in a sterile condition or it may be any suitable liquid swelling medium. The swelling may also be initiated already before packaging of the catheter, the catheter then being packed in a substantially gas impermeable package for conservation of the moistened surface. Furthermore, the liquid swelling medium may be provided in a capsule or container directly within the hose member together with the catheter for swelling of the hydrophilic material immediately prior to the insertion.

It is an advantage to provide the catheter package in a material which is at least substantially gas and water impermeable, which is durable to at least moderate external conditions, such as temperature variations and light. The material should at least substantially maintain its properties over a period of up to 12 or more months, e.g. up to 24 month or even more. The catheter package, including the applicator, the closure(s) and other parts of the package or at least the hose of the package could therefore preferably be made from silicone or a thermoplastic elatomeric material, other thermoplastic materials, curable elastomeric materials, polyamide resins or elastomers or any mixture thereof, i.e. the group may comprise materials like, PA, PP, PVC, PU, PE, EVA, latex, and/or Kraton™. All parts of the catheter package may be made from two foils of a sheet material joined along edges, e.g. by welding or gluing or in any other way by adhesively bonding the foils together or the package may be made from an extruded substantially tubular member being closed in both ends. A foil may advantageously be made from laminates of different materials. One layer may e.g. be a layer of aluminium or similar metal for provision of a completely gas-impermeable package. Another solution is to apply aluminium either to a surface of the package material or to apply aluminium within the material, e.g. laminated between layers of a elastomeric or thermoplastic material.

The proximal end and the distal end of the catheter package could be provided with an even structure. However, it will be preferred that the proximal end of the package is provided with opening means adapted to remove the proximal end of the catheter. Similarly, the distal end of the package may be provided with opening means adapted specifically for draining fluid substances from the package. The fluid substances may either be a friction-reducing medium or urine.

Preferably, the hose member is an elongate and/or tubular member adapted to accommodate at least a major part of the catheter. If the catheter is of the kind which develops a low friction surface character upon treatment with a liquid medium or substance, it may be an advantage to provide the liquid medium in the package and preferably in the hose member. The catheter will thereby be treated already upon removal of the catheter from the package. For this purpose, the hose member may preferably be adapted to relatively closely enclose the catheter. As an example, the inner diameter of the hose of the package may preferably be in the range of 1.005–3 times the outer diameter of the catheter, such as 1.0–1.9 times, such as 1.3–1.8, such as 1.4–1.7, such as 1.5–1.6, such as in the size of 1.55 times the outer diameter of the catheter. Alternatively, the liquid medium may be contained in a pouch or a container connected to the package. The pouch or container may e.g. constitute a closure for closing either the proximal or the distal end of the package. Preferably, the pouch or container is integrated in a closure for closing the proximal end of the package, which end is located near the proximal end of the catheter.

If the catheter is a hydrophilic catheter, i.e. if the catheter is either coated with a hydrophilic coating or made completely from a hydrophilic material, the liquid substance may be water or a water/saline solution. If the catheter is of the traditional type having a primarily hydrophobic surface, the liquid substance may be a regular lubricant.

The tubular compartment of the applicator should at least have a flexible zone but may preferably be formed entirely with a wall of a flexible material allowing the compartment wall to be brought into contact with the catheter. The compartment could be used as an applicator for guided non-contaminating insertion of the catheter into the urethra. The tubular compartment define either a curved or a substantially linear passage extending through the compartment and ending in an open end-part or the passage could be curved in one section and substantially linear in another section. As an alternative, the hose may be formed partly with a wall of a flexible material so as to allow the hose wall of the flexible part to be brought into contact with the catheter. In that case, the applicator may be reduced to a tubular compartment with a first open end, the compartment being adapted to receive at least a part of a catheter and comprising clamping means adapted to apply a pressure to the outer surface of the wall of the hose. This will allow a user of the assembly to use the hose itself as an applicator for guided non-contaminating insertion of the catheter into the urinary canal. The applicator merely being provided for applying a sufficiently strong force to the outer surface of the hose for bringing the inner surface of the hose in contact with the catheter.

The tubular compartment should surround the catheter and should be open in both end zones thus allowing the utensil to extend out of the end zones. The compartment may have any cross-sectional shape, e.g. circular, and any wall-thickness distribution, e.g. even wall thickness throughout the compartment, or parts of the compartment wall may be provided with relatively large wall thickness compared with other parts of the compartment wall. However, a substantially circular cross sectional shape of the compartment typically matches the cross-sectional shape of most catheters and supports for a good grip.

The compartment should be provided with a radial size so that a clearance is defined between the inner surface of the compartment and the outer surface of the catheter so that the catheter is allowed to slide back and forth inside the compartment. The clearance does not need to be of equal size throughout the compartment, but may be larger near the end portions and narrowing down towards the intermediate portion of the compartment. The compartment could be asymmetrically formed in relation to the intermediate part, e.g. so that one end portions narrows down whereas the other end portion is of equal size or narrows down with a different slope rate. However, the size of the compartment should allow the compartment to be axially positioned along the catheter, i.e. the internal radial size of the compartment should at least be slightly larger than the outer radial size of the catheter in question.

During use, the applicator is arranged around the catheter in question and the compartment wall is brought into engagement with the catheter by use of the clamping means. If the catheter is a urinary catheter, the user may grip the proximal, insertable, catheter end by bringing the wall of the compartment into contact with this part of the catheter and guide the catheter tip into the urinary canal. Subsequently the grip may be released while the applicator is shifted to a new position further down towards the distal end of the catheter. The catheter is again gripped and the next section of the catheter is inserted. This is continued until urine starts to drain out of the distal catheter end.

The clamping means may either be provided in the form of a weakened zone of the compartment allowing the compartment to kink and thus the wall to be brought into engagement with the catheter or by squeezing the outside of the compartment with other forms of clamping means.

Kinking of the compartment may be supported by providing at least a part of the intermediate portion of the compartment with a reduced bending moment in relation to the bending moment of the end portions. This will facilitate kinking of the compartment upon application of finger pressure. The kinking will cause the compartment wall to be brough into engagement with the outer surface of the catheter and thus provide an increased friction between an inner surface of the compartment and an outer surface of the catheter.

The reduced bending moment may e.g. be obtained by providing the intermediate portion with a smaller radial size than the end portions, by providing the intermediate portion with a smaller wall thickness than the end portions, by providing the intermediate portion in a material which is different from the material of the end portions or by any combination of the mentioned methods. Moreover, the reduced bending moment may be obtained by providing a notch e.g. in the intermediate portion. The notch may be formed substantially perpendicular to the axial direction and preferably in the outer surface of the applicator. Preferably the notch is applied in the form of a circumferentially extending groove or depression into the outer surface of the intermediate portion of the compartment. By reducing the bending moment of the intermediate portion in any of the above mentioned ways, it may easily be obtained that the compartment kink or collapse upon application of finger pressure. In particular, such a compartment will be sensitive to an axial compression of the compartment, which may easily cause the compartment to kink. Likewise, application of a radial pressure on the intermediate portion simultaneously with the application of an oppositely directed radial pressure on the end portions may easily cause the compartment to kink.

An enhanced fixation of the catheter within the applicator may be achieved by forming the applicator with a wail having inwardly extending gripping means adapted to engage the catheter when the compartment kinks. The gripping means could be provided in the form of one or more resilient bulges extending inwardly into the compartment or the gripping means could be provided in the form of a relatively hard or sharp edge or ring extending inwardly in the compartment. The use of resilient vanes may provide a compartment which softly approaches the catheter and increases the friction therein between, whereas a sharper edge will enable a stronger grip e.g. by pressing a notch into the surface of the catheter. The gripping means may be provided in one or both of the end portions and/or in the intermediate portion, e.g. in the vicinity of one or both of the ends or in the vicinity of the weakened zone, e.g. one each side of the weakened zone.

Especially the disabled user may find difficulties in applying a radial pressure on the intermediate portion simultaneously with the application of an oppositely directed radial pressure on the end portions or by axially compressing the compartment. In order to facilitate a better handing of the applicator, outwardly extending handling means may be arranged at the first and/or the second end portion(s) of the compartment.

In order to further facilitate an eased handling of the applicator, the distance between the handling means may preferably be in the range of 30–150 mm., such as in the range of 40–130 mm., such as in the range of 50–100 mm., such as in the range of 60–90 mm., such as in the range of 70–80 mm., such as in the size of 75 mm.

In order further to facilitate a better handling, the outer radial size of the applicator compartment may preferably be in the range of 4–20 mm. such as in the range of 8–18 mm., such as in the range of 12–16 mm., such as in the size of 14 mm. The radial size of the handling means may preferably be in the range of 1,5–4 times the outer radial size of compartment, such as in the range of 2 times the outer radial size of compartment.

According to a preferred embodiment, the clamping means are adapted to apply a squeezing pressure against the outer surface of the compartment wall so as to press the inner surface of the wall into engagement with the outer surface of the catheter. Accordingly, the clamping means may be provided with a first handle member joined to the applicator at a first pivot point allowing the handle member to be biased against the outer surface of the compartment wall so as to squeeze the inner surface of the wall into engagement with a catheter arranged therein. The handle and the first pivot point could be formed cost efficiently as an integrated part of the applicator as the applicator may be moulded in one piece. The applicator may be made from various metallic or plastics materials but preferably from silicone or a thermoplastic elatomeric material, other thermoplastic materials, curable elastomeric materials, polyamide resins or elastomers or any mixture thereof, i.e. the group may comprise materials like, PA, PP, PVC, PU, PE, EVA, latex, and/or Kraton™.

A second handle member may be joined to the applicator at a second pivot point allowing the handle member to be biased against the outer surface of the compartment wall so as to squeeze the inner surface of the wall into engagement with a catheter arranged therein. The second handle member could be arranged in relation to the first handle member so as to bias against an opposite site of the outer surface of the compartment. In that way, the catheter may be gripped in a fashion similar to a wire between flat-nose pliers or forceps.

In order to further increase the pressure from the handle members against the outer surface of the compartment wall and thus against the catheter in question, the first handle member and/or the second handle member may further comprise a jaw-portion arranged on the handle member to engage the flexible zone of the compartment wall when the handle member is biased against the outer surface of the compartment wall. According to one embodiment, the jaw-portion may connect the handle member with the surface of the compartment wall. The handle member, the jaw-portion and the compartment wall may e.g. be moulded in one single piece.

In order to provide a high pressure squeezing against the utensil, the jaw-portion should extend substantially perpendicularly from the corresponding handle member. The jaw-portion may have any cross-sectional shape and the surface portion of the jaw, which is to be pressed against the compartment wall may either be triangularly or sharp-edged, circularly shaped with a soft curvature facing the compartment wall or the surface may be flat ("non-sharp"). The use of sharp-edged tip may on one hand enhance the ability to grip even a slippery catheter but on the other hand, there is a risk that the pressure from the sharp tip may cause embossing marks in the surface of the catheter. The wall thickness of the flexible zone or of the entire compartment may be kept low. By selection of an adequate material, e.g. a silicone rubber, the wall thickness of at least the flexible zone may be kept down to the order of 0.01 mm. As an alternative, the flexible zone may be provided with a wall thickness which is relatively larger than the wall thickness of the surrounding part of the tubular compartment of the applicator. This will allow the zone to be pressed against the catheter in a more soft and protective way without destroying the surface of the catheter. As another alternative, the zone, on which the clamping means applies a pressure, may be less flexible than the surrounding part of the tubular compartment of the applicator. As the clamping means applies the pressure, this wall part will press against the catheter. Due to the less flexible structure of the surface zone, the pressure will be distributed more evenly over the entire zone and therefore the tendency of destroying the catheter surface may be reduced. The entire wall of the tubular compartment of the applicator may thus also be provided with an even wall thickness and with the same flexibility throughout.

In order to allow the user more easily to manipulate the catheter in a direction along a first axis extending through both of the openings of the tubular compartment, the compartment may preferably be provided with a first flange extending radially from the tubular compartment. This direction is transverse to the direction of the catheter and thus to the direction in which the catheter is to be guided into the bodily canal.

In order further to improve the manoeuvrability and to allow the user more easily to manipulate the compartment in both directions along the first axis, the compartment may, be provided with a second flange extending radially from the tubular compartment. A specifically ergonomic applicator may be provided when the distance between the two radially extending flanges allows at least one or two adult fingers to grip the applicator between the protruding flanges. It has thus been found that a convenient length between the two flanges is in the range of 20–150 mm. such as in the size of 35 mm. The one or two handle members may preferably be arranged between the flanges. According to a preferred embodiment, the handle members may extend from a pivot point substantially where one of the two flanges protrudes.

According to a preferred embodiment, the flanges are oval or rectangular or at least noncircular in shape so that each of the flanges protrudes mainly in one or two radial directions from the tubular compartment. In that respect, one of the flanges may preferably be rotated in relation to the other of the flanges around the first axis. If a first of the two flanges is rotated in the order of 90 degrees around the first axis in relation to a second of the flanges, the user may conveniently grip the utensil or applicator in a firm handgrip and slide the hand in one direction across the one of the flanges until the hand catches the second flange and the sliding is stopped by that flange. By rotating the utensil or applicator 90 degrees within the handgrip, the user may slide the handgrip in the other direction along the utensil or applicator, past the second flange, until the hand catches the first flange and the sliding is stopped by that flange.

The flanges may be arranged in the vicinity of respective open end parts of the compartment.

In order further to improve the grip of the catheter and in order to establish the grip upon the slightest depression of the wall of the applicator, the inner surface may be provided with one or more protrusions extending radially inwardly. The radial distance between at least one point on the inner surface of the tubular compartment of the applicator and the outer surface of the catheter may be low compared with the overall radial distance between the inner surface of the applicator and the outer surface of the catheter. The protrusion, likewise the jaws, may have any shape, e.g. a curved shape or a sharp or flat edged shape against the catheter. As an alternative, the protrusion may be replaced with a ring-shaped inwardly extending elevation of the inner surface of the compartment.

In order to allow easy manipulation of the catheter, the applicator may be detachably attached to a first end of the hose and preferably to the proximal end thereof. That will allow the user to grip the proximal end of the catheter and insert it into the urethra during simultaneous removal of the catheter from the package.

In order further to facilitate the simultaneous insertion and removal of the catheter from the package, the hose may be provided so that the user, during the removal and insertion, can vary the length of the hose. This will allow the user to contract the hose for exposing the proximal end of the catheter through the catheter outlet.

The variable length may be provided by a telescopic arrangement of a first part of the hose in relation to a second part of the hose. Alternatively, at least a first part of the hose member and preferably the part enveloping the proximal end of the catheter, may be formed with a concertina folded wall. This will allow the length of the hose wall to be extended and shortened respectively which again will facilitate easy removal of the proximal end of the catheter from the hose member. As an example, the proximal end of the catheter may be enveloped in the hose member. In order to be able to squeeze the compartment of the applicator into contact with the catheter, the user will first have to move the catheter out of the hose member and into the compartment. With the concertina folded wall of the hose member, the user may simply press the compartment against the concertina folded hose member. The length of the hose member is thereby reduced and the proximal end of the catheter is moved into the compartment. The user may now grip the catheter through the compartment wall and thus pull the proximal end of the catheter out of the catheter package without touching and thereby possibly contaminating the catheter.

The package may preferably be closed in the proximal end by a detachable closure, e.g. by a thin foil adhesively bonded to an opening of the proximal end of the package. This will allow the user to open the proximal end of the package by pushing the proximal end of the catheter though the foil, thereby letting the foil be penetrated by the catheter tip. After removal of the closure, the user may draw the proximal catheter end out of the compartment, e.g. by squeezing the compartment into contact with the catheter and by contracting the length of the hose.

So as to avoid contamination of the surroundings after the catheterisation, the detachable closure may preferably be provided so that it can be re-connected to the compartment after catheterisation, thus leaving at least the proximal end of the package closed.

In order further to facilitate easy access to the catheter when the closure is removed from the package, the closure may preferably be provided with a cavity with a first open end, the cavity being adapted to receive at least a part of a catheter which extends out of the package. When the package is closed, the catheter or any other oblong medical utensil extends out of the package and into the cavity of the closure. When the closure is removed, the tip, e.g. the proximal insertable end of the catheter extends out of the package, which makes the catheter easy accessible for the user. As an example, the tip of the catheter which extends out of the package may be gripped by means of an applicator and guided to the urethra or to a similar urinary canal.

In order not to lose the detachable closure, the closure may be provided with a strap connecting the closure to the package when detached. As an example, the closure may be connected to the applicator or to the hose or to any other part of the package.

In order to provide a catheter assembly which is uncomplicated to use even for persons with a reduced dexterity, the closure may be provided with a gripping zone for easing the grip and thus the opening or re-closing of the package.

The gripping zone may be provided as a radially extending flange or flanges of the closure or as a zone or zones of the closure having a large outer cross sectional diameter. The closure may also be provided with means for engaging an external handle. As an example, the closure may be provided with a ring-shaped bulge for attaching a handle. Preferably, the gripping zone is provided in the form of a handling tab extending in the direction in which the closure is intended to be removed from the package. The handling tab could be provided as a soft resilient strap enabling the user to remove the closure by use of the mouth.

The connection between the applicator and the hose and/or the connection between the package and the closure may be provided so that the connection can be re-established by twisting and/or pushing one of the parts onto the other of the parts to be connected.

The second compartment may be provided with a weakening line for opening the first end by tearing off a first end part of the compartment.

In some situations, the user may want to use the catheter without removing the catheter completely from the package. As an example, the user may want to use the package to make the catheter longer, e.g. for reaching to a sanitary arrangement. Since there is a clearance between the inner surface of the catheter package and the outer surface of the catheter itself, urine may flow backwards in the package in a direction opposite to the flow direction inside the catheter. An unwanted situation is that the user of the catheter and/or the surroundings gets contaminated by urine or other liquid substances, e.g. a lubricant or a swelling medium for a hydrophillc catheter applied to the catheter for the purpose of reducing the surface friction.

According to a preferred embodiment, sealing means adapted to provide a substantially liquid tight seal between the catheter package and the urinary catheter, while the catheter is being dispensed from the package is provided. The sealing means may be provided in the proximal end of the package, e.g. constituting a closure for the proximal end of the package. As an example, the closure may have a rupturable portion with a shape which matches the outer cross-sectional shape of the catheter. When the catheter is removed through the rupturable portion, the closure will sealingly surround the catheter while the catheter is being dispensed from the package. The cavity defined between the hose of the package and the catheter is thereby defining a receptacle. The receptacle may e.g. be used for storage of a friction-reducing substance.

The sealing means may also be arranged between an outer surface of the urinary catheter and an inner surface of the hose. As an example, the sealing means may be provided in the form of a sliding seal adapted to move in relation to either one of the inner surface of the hose, the outer surface of the catheter or both, while still providing a substantial liquid tight passage therein between. The cavity of the hose thereby defines an upper receptacle located near the proximal end of the package and an oppositely located lower receptacle between the catheter and the hose. Especially the upper receptacle may advantageously be used for storing a friction reducing substance for treatment of at least the proximal end of the catheter in the package.

The sealing means could be provided in the form of an obstruction which substantially prevents a liquid substance to pass between the inner surface of the package and outer surface of the catheter. The sealing means thus divides the space confined between the catheter and the hose member into an upper receptacle, in the direction towards the proximal end of the catheter and package and a lower receptacle, In the direction towards the distal end of the catheter and package.

As an example, the sealing means could be provided as a radially outwardly extending protrusion of the outer surface of the catheter or as an inwardly extending protrusion of the inner surface of the hose member, e.g. in the form of a resilient vane adapted to contact the inner surface of the hose member or outer surface of the catheter, respectively. The outwardly extending protrusion of the catheter should in this respect be understood either as a protrusion connected to the catheter or a protrusion formed directly on the surface of the catheter. As an example, the catheter may be connected with a plug member, which plug member is provided with vanes adapted to slide along the inner surface of the hose or at least parts thereof. Similarly, the inwardly extending protrusion of the hose should be understood either as a protrusion connected to the hose or a protrusion formed directly on the inner surface thereof.

Two or more radially outwardly or inwardly extending protrusions of the outer or inner surfaces of the catheter and/or the hose member, will provide an even better sealing against flow of liquid substances between the two compartments. By providing the at least two radially inwardly extending protrusions of the inner surface of the hose member with different radial sizes, a further sealing effect will be achieved.

According to a preferred embodiment, the sealing means comprises a ring-shaped member arranged between the inner surface of the hose member and the outer surface of the catheter. As an example, a regular ring-shaped gasket may be placed inside the hose member. Preferably, the member is loosely arranged so that it is allowed to move back and forth inside the hose. As an example, the ring-shaped member may be provided with a clearance against the hose member and against the catheter so that liquid substances are substantially prevented from passing the ring-shaped member and so that the ring-shaped member is still allowed to be shifted longitudinally back and forth in the catheter package.

The ring-shaped member may preferably be adapted to co-operate with an inwardly extending protrusion of the inner surface of the hose member or with an outwardly extending protrusion of the catheter.

The distance from the distal end of the urinary catheter to the position of the sealing means may preferably be provided between 0 and 100% of the total distance between the distal end of the catheter and the proximal end of the catheter, such as 0%, such as 10%, such as 20%, such as 30%, such as 40%, such as 50%, such as 60%, such as 70%, such as 80%, such as 90%, such as 99%.

In general, the problems of introducing a catheter into urethra depend not only on the size of the introduced part of the catheter but also on the slipperiness of the introduced part. As previously mentioned, the catheter or at least a part of the catheter adapted for insertion into urethra or an artificial urinary canal may often be provided with a surface slipperiness for easy and safe insertion. However, it has been found that the slippery surfaces are difficult to handle, not least for a user having reduced dexterity. It is therefore an important aspect of the present invention to allow the user to manipulate the catheter by touching only the catheter package and only to expose a length of the catheter which is necessary for opening the bladder. Preferably, the sealing means is arranged so as to seal between the outer surface of the catheter and the inner surface of the hose over a certain dismantling length. This will allow the user of the catheter to withdraw the catheter at least partly from the package, e.g. by pulling the proximal end of the catheter out of the catheter package, meanwhile the sealing between the catheter and the package remains. The feature allows that a catheter type of one length can be supplied both to male and female users. The user only needs to withdraw a length of the catheter from the catheter package necessary for opening the bladder, i.e. approximately 50–90 mm. for female users and approximately 180–250 mm. for male users. The entire length of the catheter may be up to 350 mm. or even more. Moreover, the entire length of the catheter may be adapted to be dispensed from the package. Thereby, the user will have a chance to discharge urine or other liquid substances from the package more distantly from him.

The sealing means and/or the hose member may preferably be provided so that a passage is defined between the outer surface of the catheter and the inner surface of the hose member while the catheter is being dispensed over a first dispense section, thus preventing fluid from passing between the urinary catheter and the hose member when the sealing means is positioned within said first section.

In order not to contaminate the surroundings with friction-reducing substances, it is an advantage to allow such a substances which may possibly be stored in the upper receptacle to drain down into the lower receptacle before dismantling the catheter through the proximal end of the package. The sealing means and/or the hose may therefore preferably be provided so that a clearance is defined between the outer surface of the urinary catheter and the inner surface of the hose member over a second dismantling section, thus allowing a fluid to pass between the urinary catheter and the hose member when the sealing means is positioned within said second section. As the catheter is being removed from the package, the catheter enters the second dismantling section. Any liquid substance contained in the upper receptacle is thereby drained down into the lower receptacle and it is thereby avoided that the substance unfortunately is released through the proximal end of the package.

The length of the first dismantling section may preferably constitute between 0 and 100% of a total length of the package, such as 0%, such as 10%, such as 20%, such as 30%, such as 40%, such as 50%, such as 60%, such as 70%, such as 80%, such as 90% or such as 100%.

According to one embodiment, the hose is provided with an internal surface which is tapered so that the internal clearance of the hose is increasing from a first internal clearance in one end to a second internal clearance in the opposite end, the first internal clearance providing a substantially liquid tight seal between the internal surface of the hose and the catheter and the second internal clearance providing a liquid flow channel between the internal surface of the hose and the catheter.

According to one embodiment, the substantially liquid tight seal is provided continuously between the catheter package and the catheter over the first dispense section. However, the liquid tight seal may also be provided discontinuously.

In order to ensure, that the catheter stays in the withdrawn position, i.e. to avoid that the catheter slides back into the package during the insertion or catheterisation, a locking arrangement may preferably be provided to lock the catheter into a locked position in relation to the package. The locking arrangement may be formed as a radially outwardly extending flange or protrusion arranged on the catheter for engagement with a depression in the inner surface of the hose or for engagement with a radially inwardly extending flange or protrusion arranged on the inner surface of the hose.

If the user only removes the proximal end of the catheter from the package during the catheterisation, an unwanted situation may occur if the user forgets to open the other end of the catheter package. An amount of urine may thereby build up in the catheter package and possibly cause a back-flow in the catheter tube. In this case there is a risk of severe contamination of the surroundings and also a possibility of back-flow into the bladder.

It is therefore an advantage to provide the package with an opening for draining a liquid substance out of the package. The opening may not only be used for draining urine out of the package but also for draining out surplus frictional reducing substances stored in the package for easing the insertion of the catheter, e.g. a liquid swelling medium for a hydrophilic catheter.

The opening is preferably provided in the distal end of the package since this will provide the longest distance between the proximal inserted end of the catheter and the point where the liquid substance is to be disposed, and thereby the largest degree of freedom for the user. During use, the individual may simply have to withdraw a part of the catheter which is sufficient for causing the urine to flow from the bladder. The urine will flow through the catheter conduit and into the package. The urine is allowed to drain out of the package, e.g. into the toilet or into a collection bag or reservoir connected to the package, through the opening. In accordance with the invention, the opening is closed by closing means connected to the catheter for causing opening of the package upon removal of the catheter from the package so that the user simply can not forget to open the opening. As an example, the opening may be closed by the distal end of the catheter itself.

According to a preferred embodiment, the closing means comprises a first valve member co-operating with a second valve member, the second valve member being attached to the catheter.

The first valve member may have a first sealing flange adapted for sealing engagement with a corresponding third sealing flange of the second valve member, the second sealing valve member thereby closing the outlet of the first valve member. The first and the second sealing flanges may then seal a passage between the hose and the surroundings outside the package.

The first valve member may further have a second sealing flange adapted for sealing engagement with a corresponding fourth sealing flange of the second valve member. The second and the fourth sealing flanges may then seal a passage between the conduit of the catheter and the surroundings outside the package.

According to a preferred embodiment of the invention, the closing means connected to the urinary catheter is provided with a flow channel co-operating with an outlet provided in the package. In a first position of the closing means in relation to the outlet, liquid substances are allowed to flow from the conduit of the catheter and out of the package. In another position, liquid substance is prevented from flowing from the conduit of the catheter and out of the package. The two positions corresponding to a catheter respectively taken out of the package or being taken out of the package and a catheter arranged in the package, so that the first and second valve members are engaging sealingly.

The flow channel of the closing means may further comprise at least one inlet allowing flow between one of either the lower or upper storage compartments and the conduit of the catheter. In order to prevent urine, drained through the catheter to run out trough the inlet, the inlet may be provided with means adapted to allow a liquid substance only to flow in the direction from one of either the lower or upper storage compartments and into the conduit and preferably to prevent flow in the opposite direction.

For disabled users, there may be severe difficulties in entering available toilet rooms. It is therefore an advantage to make the use of the catheter totally independent of the availability of toilet rooms by connecting a distal end of the package to a reservoir for accommodation of a liquid substance. In this case, the catheter package or at least the hose member thereof, may even be integrated in the reservoir.

It is an advantage to provide the reservoir in a material which is durable to at least moderate filling with a liquid without causing destruction of the reservoir or evaporation of the liquid substance through the walls of the reservoir. Moreover, the walls of the reservoir should at least substantially maintain its properties over a period of up to 12 or more month, e.g. up to 24 month or more. The reservoir could therefore preferably be made from a thermoplastic elatomeric material, other thermoplastic materials, curable elastomeric materials, polyamide resins or elastomers or any mixture thereof, i.e. the group may comprise materials like, PA, PP, PVC, PU, PE, EVA, latex, and/or Kraton™. Preferably, the reservoir is made from two foils of a sheet material joined along edges, e.g. by melting or gluing the foils together. The foils may e.g. be laminated from various materials and may e.g. comprise one layer of aluminium or a similarly metallic layer for providing a completely gas impermeable package.

It is an advantage if the reservoir is provided with a volume so that it will never be filled to its limit. Accordingly, the reservoir may be provided with a volume in the range of 500–5000 ml, such as 600 ml, such as 700, such as 800, such as 900 ml, such as 1000, such as 1500 ml, such as 2000, such as 2500, such as 3000 ml, such as 3500, such as 4000 ml, such as 4500, such as 5000.

It is an advantage if the liquid substances, e.g. urine, is prevented from leaking out of the reservoir. Therefore, the connection between the distal end of the package and the reservoir may be adapted to allow the liquid substance to flow only in a direction from the package to the reservoir. As an example, the connection may be provided with a back-flow valve. The back-flow valve may be integrated into one of either the first and/or the second valve members, e.g. in form of a sheet or flap allowed to be displaced from an opening between the package and the reservoir when a liquid flows into the reservoir, whereas the sheet, by means of the liquid, Is pressed back into a position wherein it blocks the passage between the reservoir and the package when liquid tends to flow in the other direction. Such back-flow valves are known in the art.

After catheterisation, many users would prefer to empty the reservoir before the catheter assembly or reservoir is disposed. It is therefore an advantage to provide a draining spout or valve for emptying the reservoir. The valve should at least be operable between a closed and an open position. As an example, the valve could be a formed as a spout with a passage which is closed. The passage may as an example be closed by melting the reservoir together along a tear-off line. After completion of the catheterisation, the user simply tears off the tip of the spout and empties the reservoir.

In some cases, the user may have to carry a used catheter assembly with an emptied reservoir until an appropriate place of disposal is available. It is therefore an advantage to provide a draining spout with a closure enabling the user, after emptying the reservoir, to close it tightly. As an alternative to a detachable closure, a valve having an open and closed position may be connected to the spout. As an example, the valve may be a regular 2-way-valve with an open and closed position.

Most catheters are provided with a surface which, when treated with a friction-reducing substance, exhibits a low friction surface character. Accordingly, it is an advantage that the package defines a liquid tight wetting pocket for treatment of the surface part with such substances. In the case the catheter is hydrophilic or at least is provided with a hydrophilic surface coating on at least the proximal end thereof, the substance would typically be a water based solution, e.g. a saline solution. If the catheter is not hydrophilic, the substance may be any regular kind of lubricant.

It is a further advantage to provide the assembly with an amount of the substance which is sufficient for effecting a treatment of at least a part of the catheter surface. As an example, the treatment may be performed on a first part of the catheter, which part is adapted for insertion into the urethra. The treatment may advantageously take place in the upper receptacle.

According to a preferred embodiment of the invention, the substance is contained in a pouch connected to the assembly. The pouch may as an example constitute a closure for closing one of either the proximal or distal ends of the package. Preferably the proximal end of the package, which end is located near the proximal end of the catheter. According to another preferred embodiment, the substance is applied to the receptacle or at least the upper receptacle during the assembling process. The low friction surface character of the catheter is thereby initiated already from the time when the catheter assembly is produced. The package is therefore preferably formed with a wall of a substantially gas Impermeable material so as to allow long time preservation of the catheter and a liquid substance in the package.

According to a second aspect, the present invention relates to an applicator for application of a medical utensil and especially of an oblong utensil in general. The applicator comprising:

a tubular compartment with a first open end, the compartment being adapted to receive at least a part of an utensil and being formed with a wall having an inner surface facing the utensil and an outer surface, the wall being provided with a flexible zone so as to allow the inner surface of the compartment wall to be squeezed into engagement with the utensil upon a pressure applied to the outer surface of the wall, and clamping means adapted to apply a pressure to the outer surface of the wall.

The applicator could have the same features as described for the applicator of the catheter assembly, and could be used for application of various utensils, e.g. for tracheal tubes, for guide wires or any kind of a catheter, e.g. for a urinary catheter.

DETAILED DESCRIPTION OF THE INVENTION

Preferred embodiments of the invention will now be described in details with reference to the drawing in which:

FIG. 1 shows a catheter assembly according to a preferred embodiment of the present invention, FIG. 2 shows an alternative embodiment of the assembly of FIG. 1, FIG. 3 shows yet another alternative embodiment of the assembly of FIGS. 1 and 2, and FIG. 4 shows an embodiment of the assembly, wherein the passage between the catheter and the hose is sealed over a first dismantling section and open over a second dismantling section, FIG. 5 shows 7 sequences of the removal of a catheter from the assembly by user of a hose with a variable length, FIG. 6 shows three different embodiments of the invention wherein the a compartment for non-contaminated insertion of the catheter into a urinary canal is attached to the hose member, FIG. 7 shows a simple embodiment of the invention, wherein the distal end of the package is closed by the distal end of the catheter itself, FIG. 8 shows an embodiment of the assembly shown in FIG. 7, wherein the distal end of the package is closed by a detachable closure, FIGS. 9–11 show three different embodiments of an assembly comprising a reservoir for storage of urine and other liquid substances.

Figure 16:
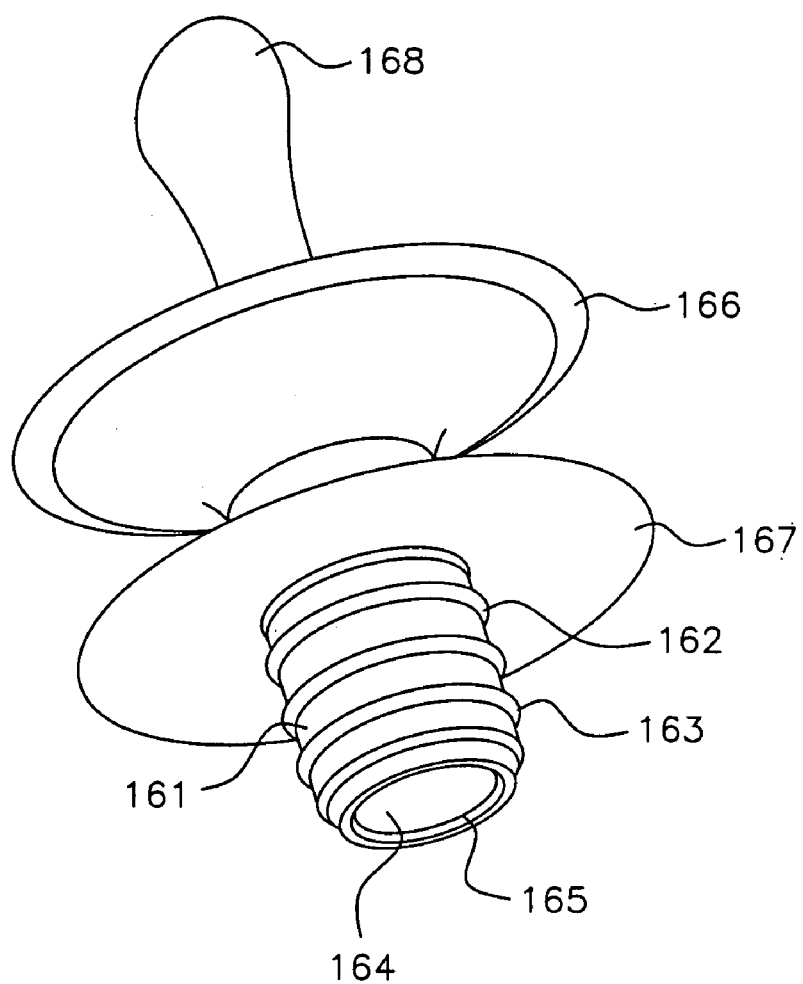
Figure 17:
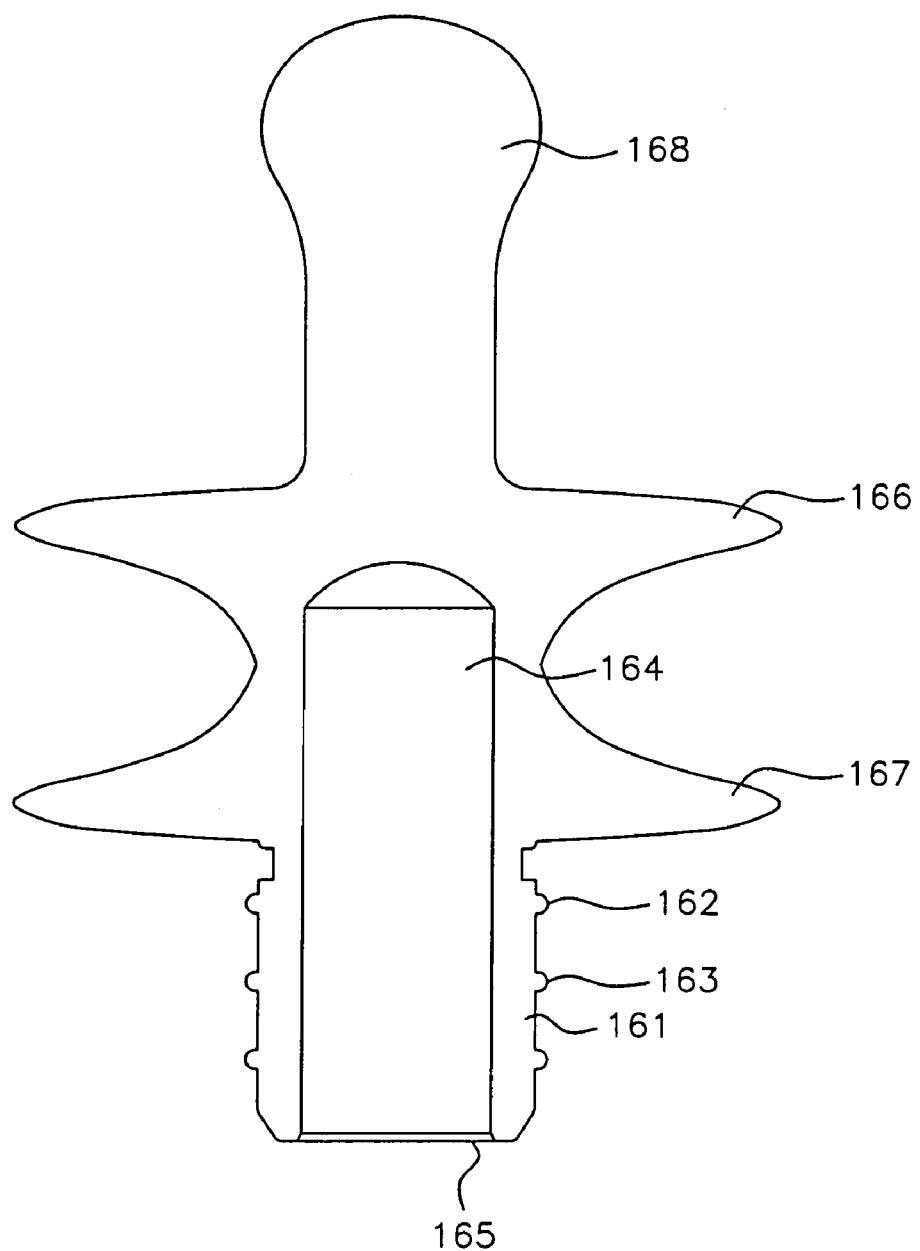
Figure 18:
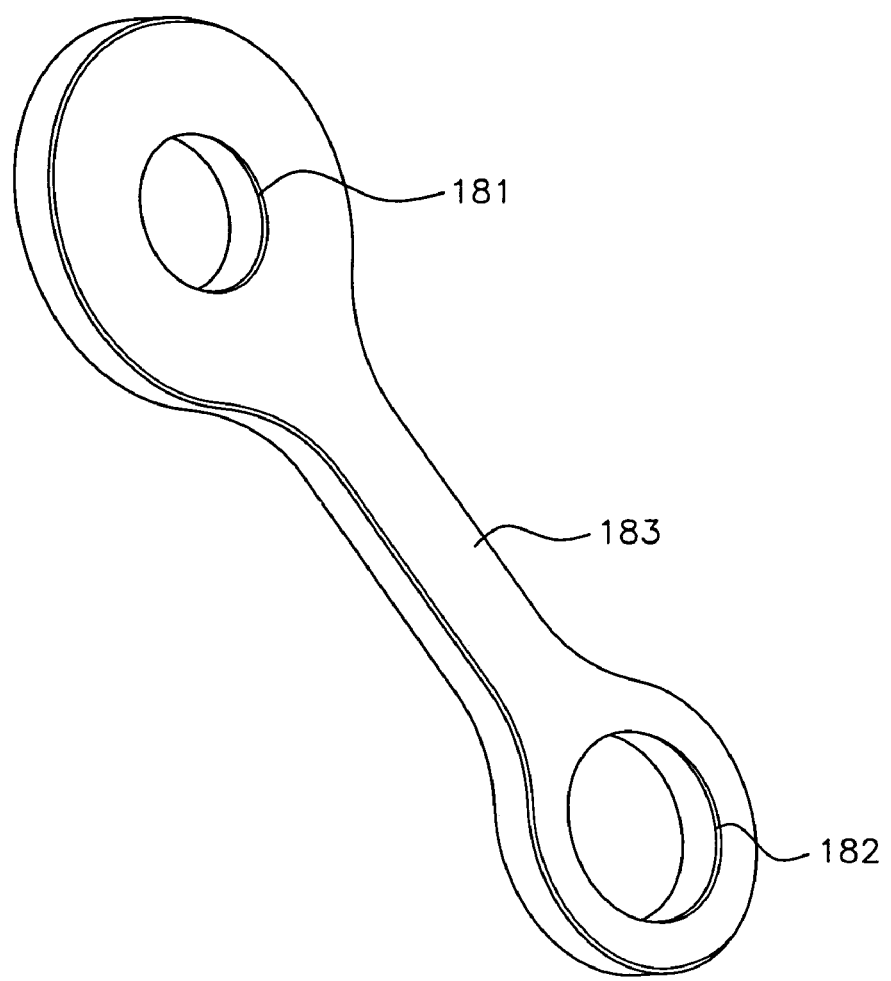
Figure 19:
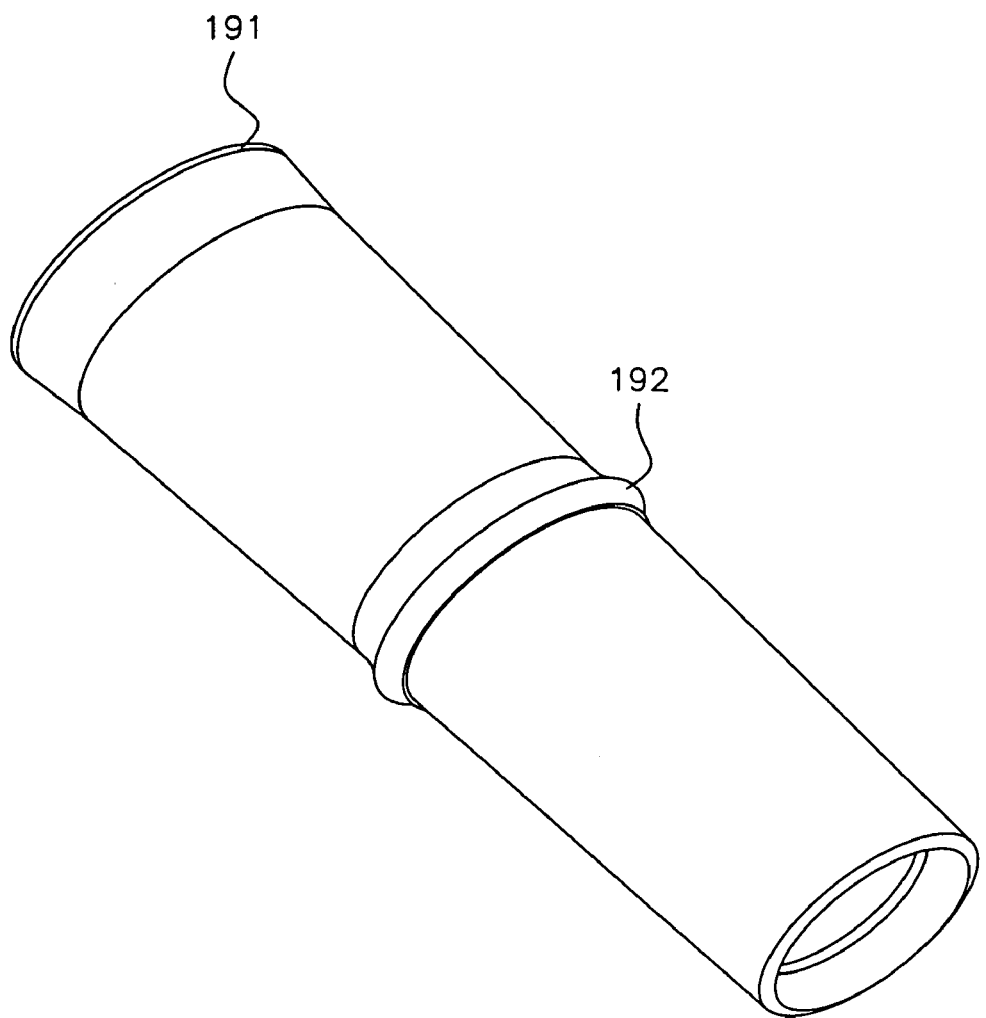
Figure 20:
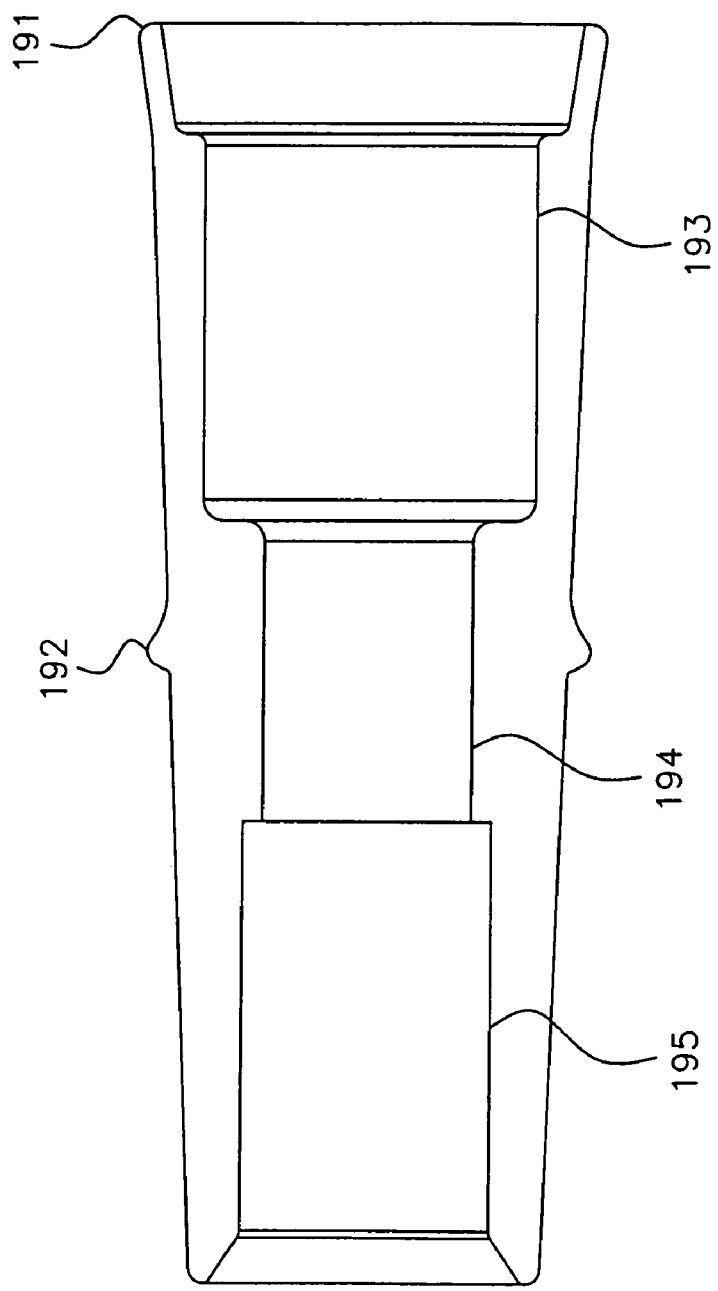
Figure 21:
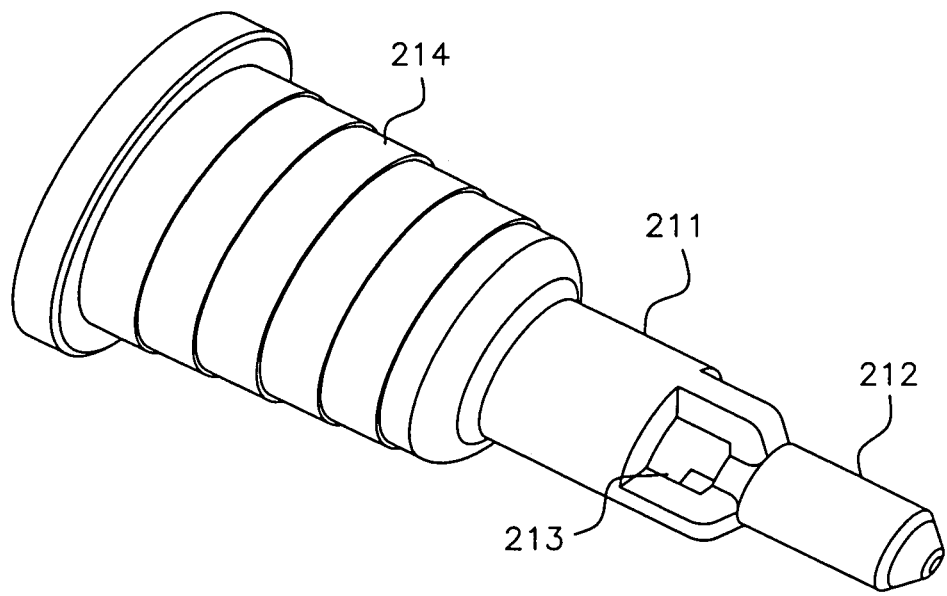
Figure 22:
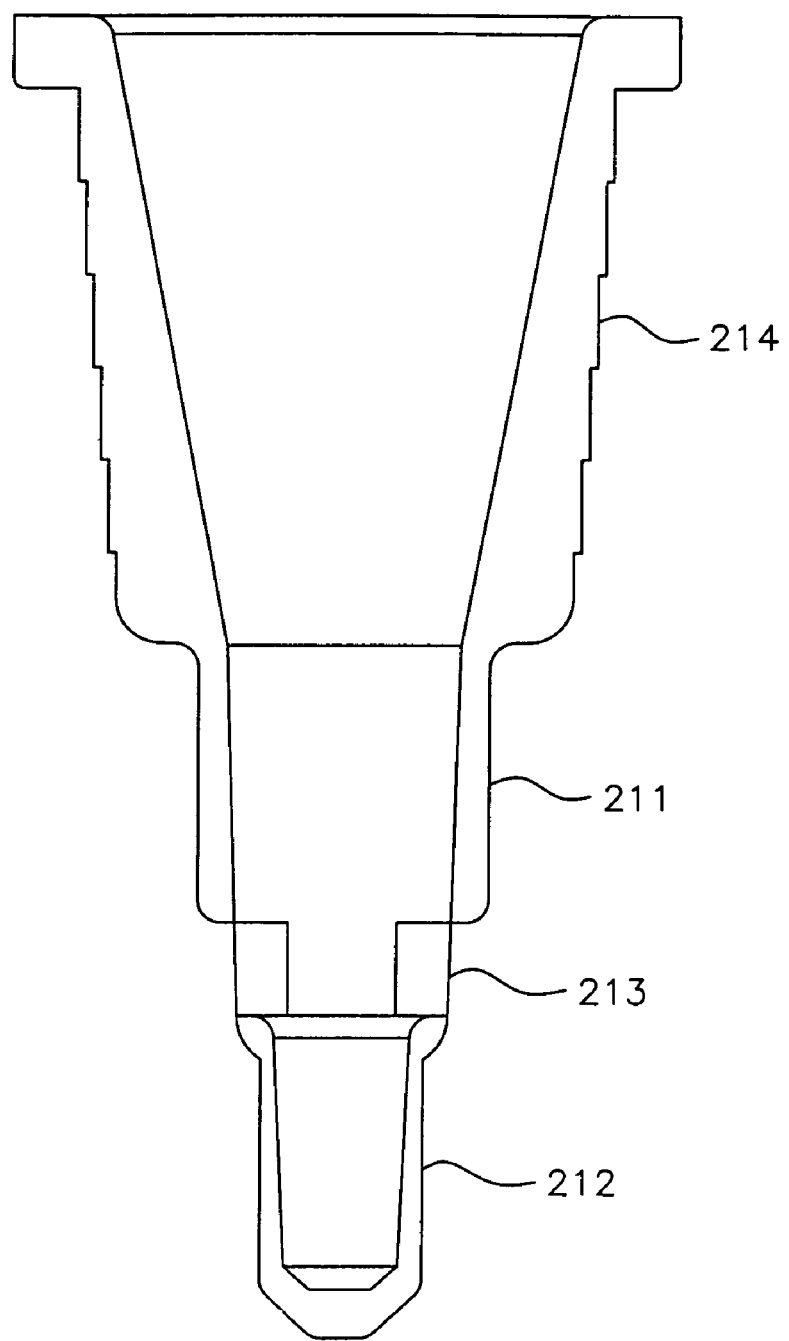
Figure 23:
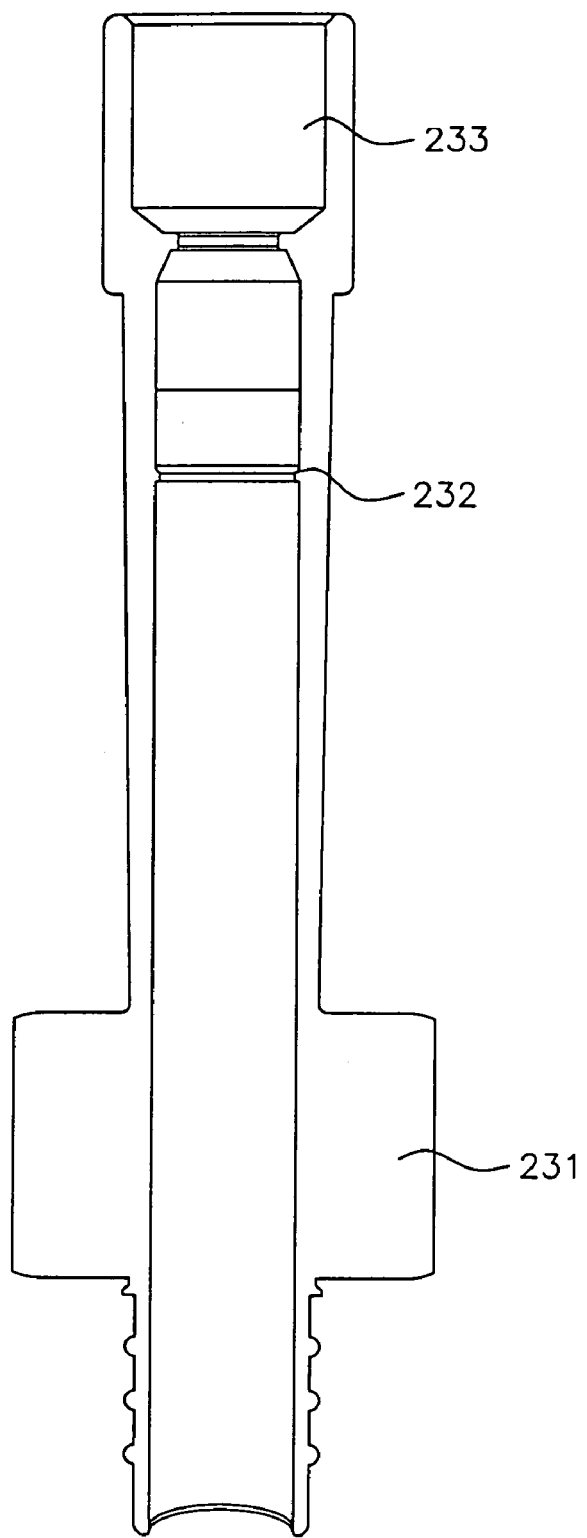
Figure 24:
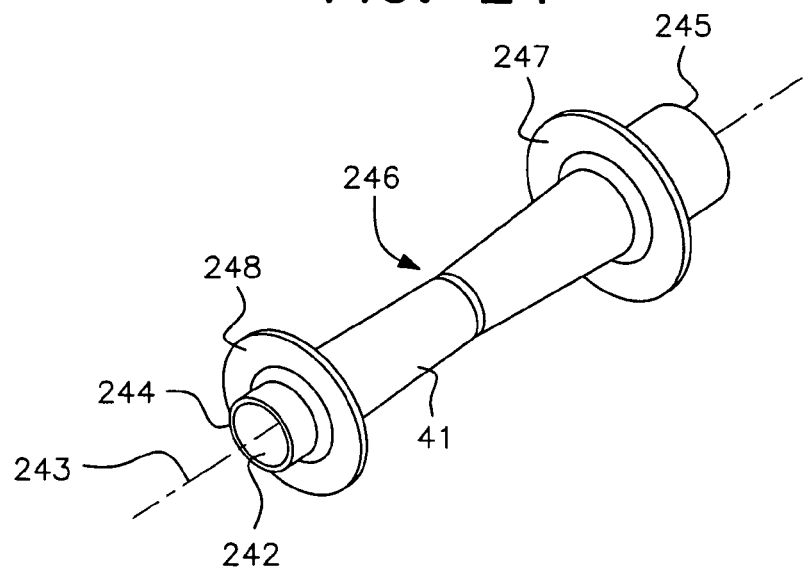
Figure 25:
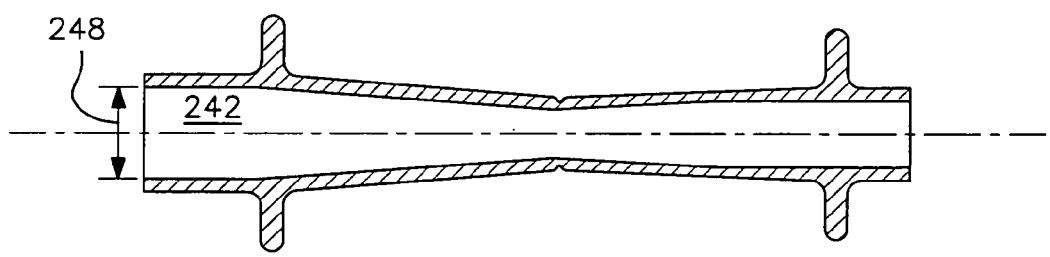
Figure 26:
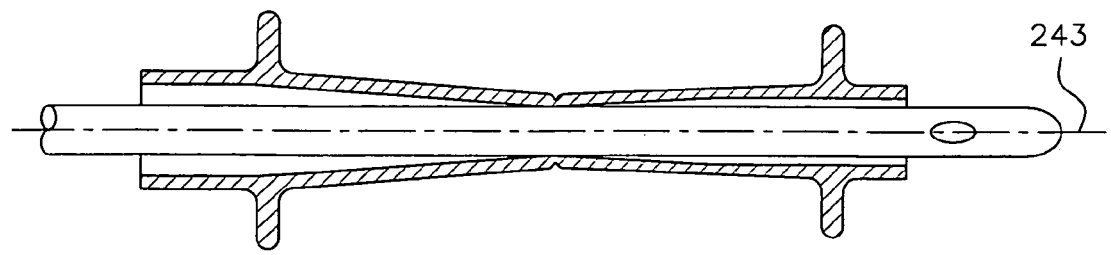
Figure 27:
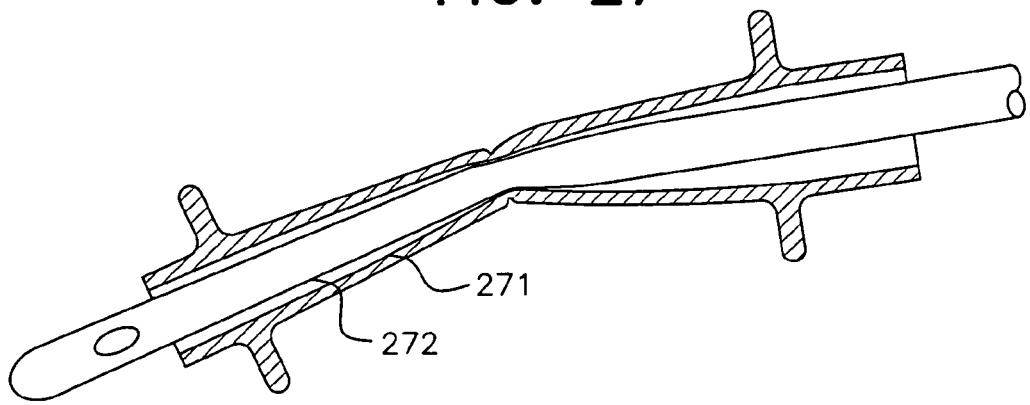
Figure 28:
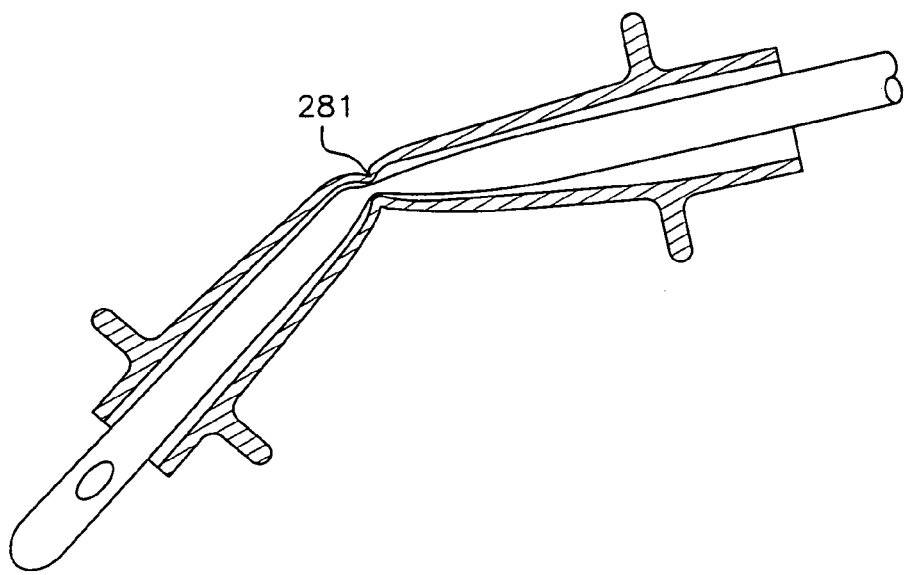
Figure 30:
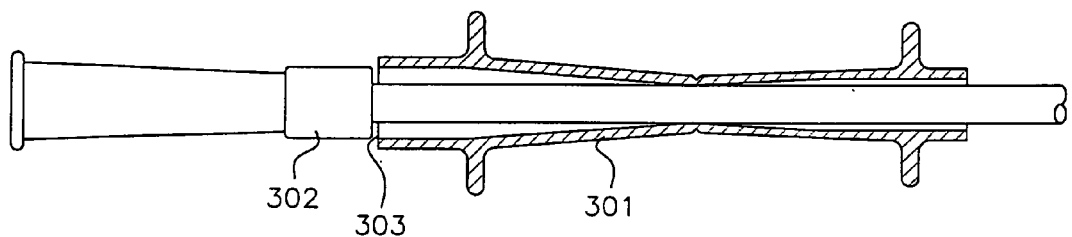
Figure 31:
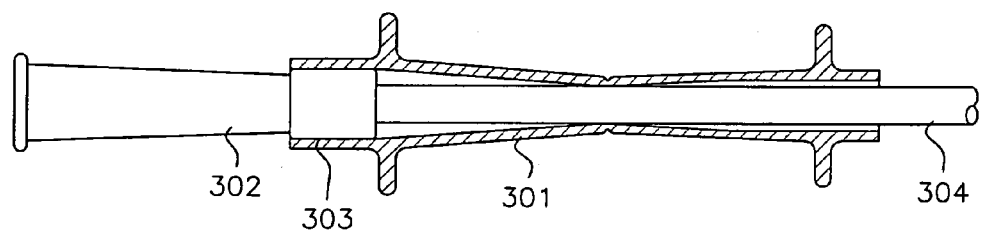
Figure 32:
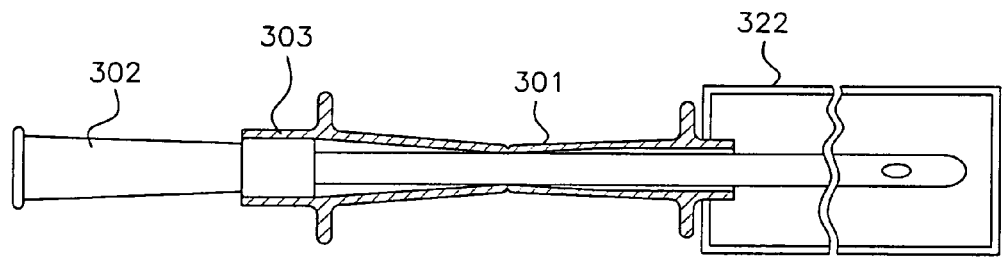
Figure 33:
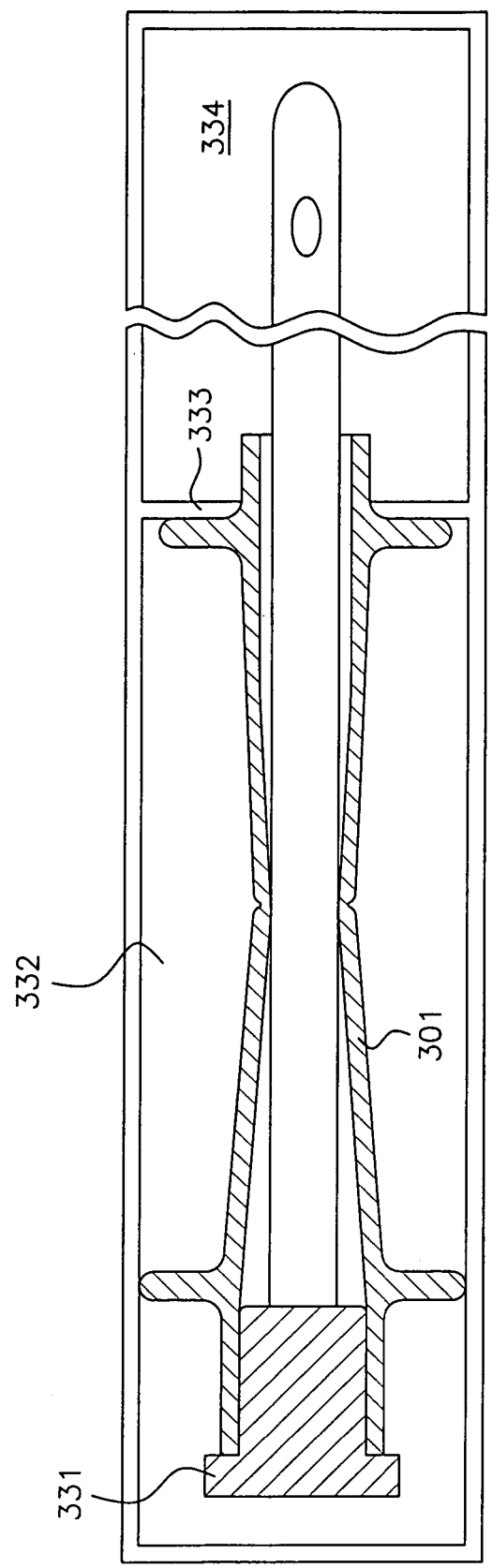
Figure 34:
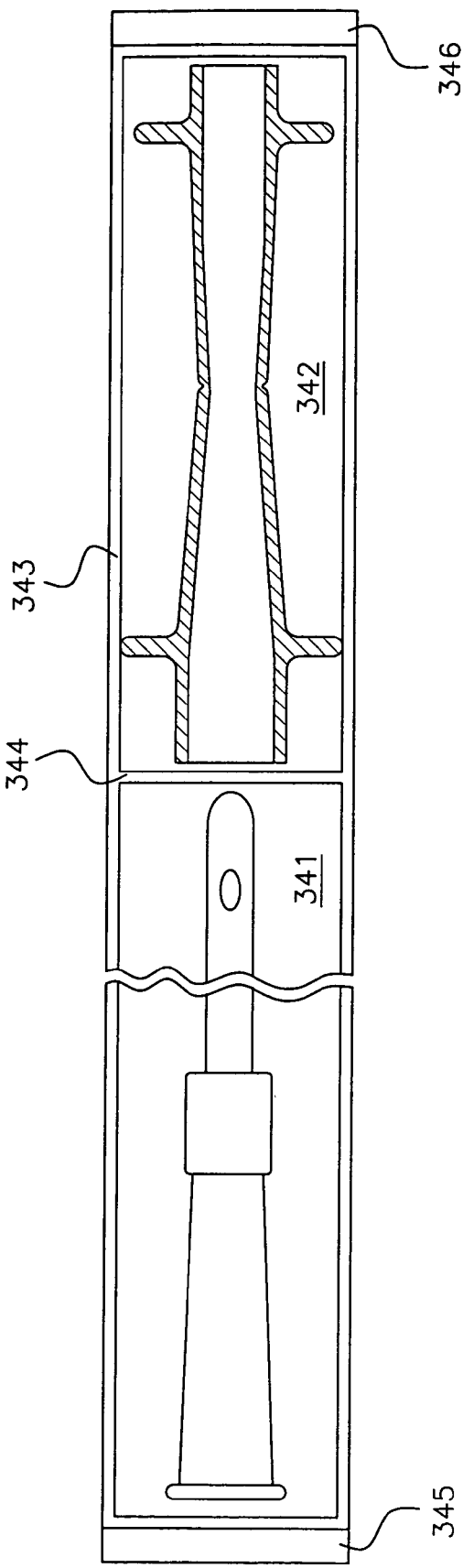

FIG. 16 shows a perspective view of a detachable closure for a package for a medical utensil, FIG. 17 shows a cross-sectional view of the closure shown in FIG. 16, FIG. 18 shows a perspective view of a strap for holding the closure of FIG. 16 attached to a package, FIG. 19 shows a perspective view of a combined valve member and a radially outwardly extending protrusion adapted to be attached to a catheter, FIG. 20 shows a cross-sectional view of the valve member of FIG. 19, FIG. 21 shows perspective view of a valve member to be fixed to an opening in the distal end of the package, FIG. 22 shows a side view of the valve member of FIG. 21, FIG. 23 shows a section of the hose provided with a diamond for bonding the hose to a bag, e.g. a urinary bag, FIG. 24 shows an applicator according to a preferred embodiment of the present invention, FIG. 25 shows a cross-sectional view of the applicator of FIG. 1, FIG. 26 shows a view of the applicator of FIG. 2, with a catheter arranged within the applicator, FIG. 27 shows a kinked applicator with a catheter, FIG. 28 shows an embodiment of the applicator in kinked position and provided with inwardly extending gripping means for enhancing the grip, FIGS. 29a–29g show various designs of the inwardly extending gripping means provided on the inside surface of the applicator, FIG. 30 shows a catheter assembly with a catheter and an applicator which are moulded to form one unit, FIG. 31 shows a catheter assembly with an applicator engaging the connector of the catheter, FIG. 32 shows a catheter assembly wherein the applicator constitutes part of the catheter package, FIG. 33 shows a catheter assembly, packed in a package, and FIG. 34 shows a catheter assembly packed in a package divided into two compartments.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Referring to FIG. 1, a catheter assembly according to the present invention comprises a urinary catheter 1 defining a conduit 2 for transportation of urine and other liquid substances, a catheter package comprising sealing means 4. In this respect the catheter is defined by a hose and by additional parts connected to the hose, e.g. the plug 25 (cf. FIG. 2). The plug combines the sealing between the catheter and the package and the closing means adapted to close the distal end of the package—see the following description. The catheter is provided with a proximal end 5, adapted for insertion into the urethra of an individual. The catheter is provided with holes 6 arranged peripherally around the proximal end part of the catheter for draining urine from the bladder and into the conduit of the catheter. The catheter is further provided with at least one opening 7 in the opposite distal end for draining liquid substances out of the conduit. The package is provided with a hose 9 defining a cavity 10 for accommodation of the catheter.

The sealing means 4 is arranged between the outer surface 11 of the catheter and the inner surface 12 of the hose member and provides a substantially liquid tight division of the space confined between the hose member and the catheter into a lower receptacle 13 and an upper receptacle 14.

As shown in FIG. 1, the sealing means may preferably be provided in the form of a radially outwardly extending protrusion 4, e.g. in the form of a soft, resilient vane of the catheter or attached to the catheter and provided in a length which enables the vane to contact the inner surface of the hose member.

Figure 1A:
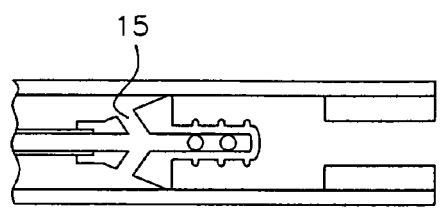

FIG. 1a shows a preferred embodiment of the assembly, wherein a flow channel 15 is provided in order to allow a liquid substance to flow from the upper receptacle 14 and into the conduit 2, e.g. water or a water/saline solution contained in the upper receptacle for treatment of a hydrophilic catheter or a lubricant for causing a low friction surface character of a conventional catheter.

Figure 1B:
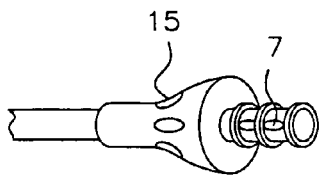

FIG. 1b shows one embodiment of the sealing means connected to the catheter.

Figure 1C:
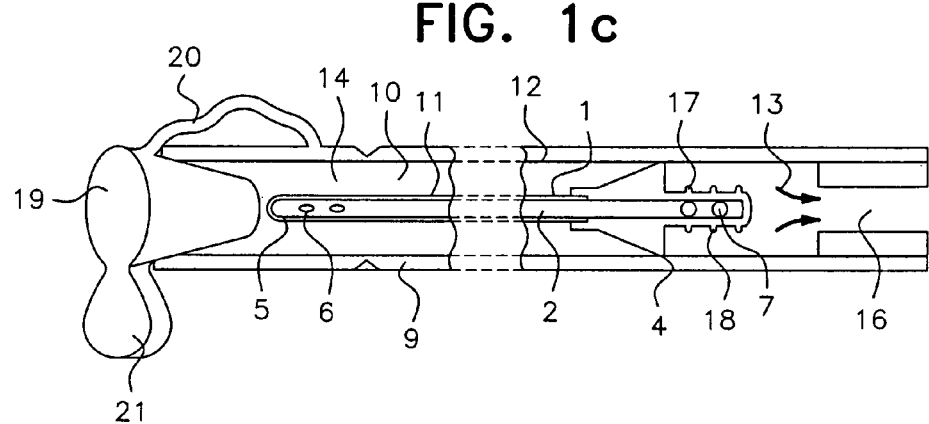

FIG. 1c shows a situation wherein an opening 16 provided in the distal end of the package, allows liquid substances comprised in the lower receptacle to drain out of the package.

Figure 1D:
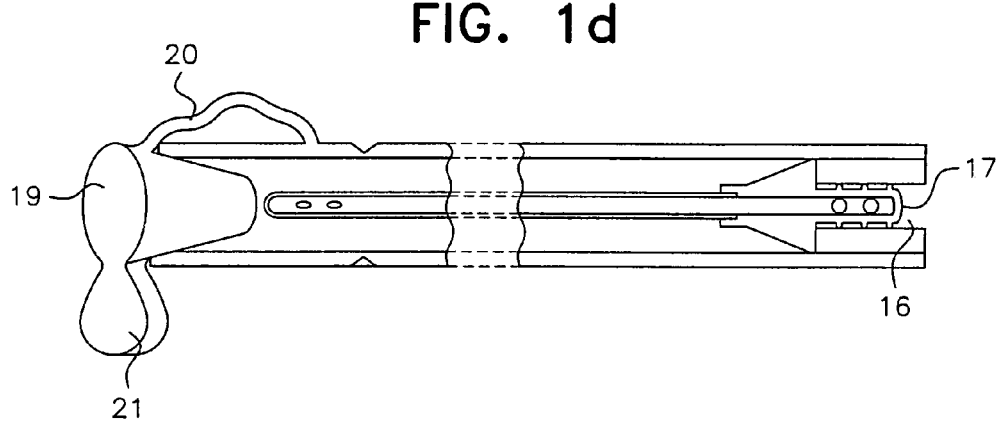

FIG. 1d shows a situation wherein closing means 17 of the catheter liquid tightly seals the opening 16. Preferably, the closing means is provided with a number of resilient and/or soft bulges 18 adapted to contact the inner surface of the opening 16.

FIGS. 1c, 1d further shows a detachable closure 19 of the proximal end of the package. The closure may, as indicated in FIGS. 1c, 1d, preferably be attached to the package via a strip 20, so that the assembly remains as one unit. The closure may be provided with a radially extending gripping handle 21, easing the removal of the closure, not least for individuals with a reduced dexterity.

FIGS. 2a, 2b, 2c and 2d shows an alternative embodiment of the plug 25 and an alternative embodiment of the distal package end, wherein an open distal end of the package is closed by a closure 26. The closure may either be detachable or glued onto the hose member 9. The plug is preferably provided with at least one outlet opening 27 allowing urine flowing from the bladder and into the proximal end of the catheter to drain out of the catheter through the plug. The plug may further be provided with an inlet 28 for draining a liquid substance from the upper receptacle 14 and into the conduit 2 for draining the substances out of the distal end of the catheter. The closure 26 is further provided with an opening 29 for draining liquid substances out of the lower receptacle, e.g. urine.

Figure 2A:
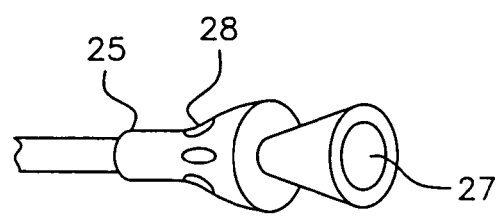
Figure 2B:
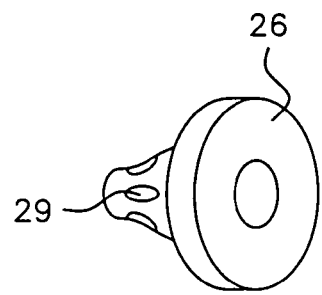
Figure 2C:
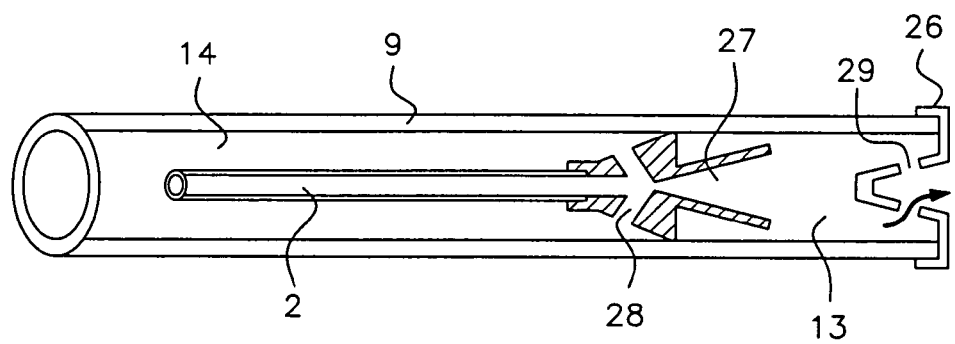

FIG. 2c shows a situation wherein the closing means of the catheter is withdrawn from the closure, whereby the passage 29 is opened.

Figure 2D:
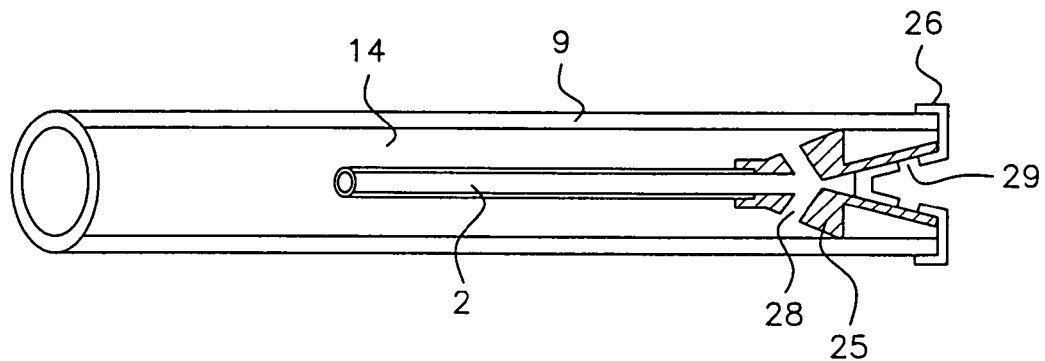

FIG. 2d shows a situation wherein the closing means of the catheter closes the passage 29 and thereby prevents a liquid substance to drain out of the package.

The catheter and package shown in FIG. 2 is not drawn in its full length. The proximal ends of both have been omitted in order to focus only on the differences between the embodiment of FIG. 1 and FIG. 2.

FIG. 3 shows an embodiment of the invention wherein the plug 35 is provided with features similar to the plug 25 of FIG. 2. The plug further comprises a groove 36 adapted to engage a ring shaped sealing member 37. The ring shaped sealing member is provided inside the package 38, either fixed to the inner surface of the hose or movably arranged so that it is allowed to slide back and fourth in the hose.

Figure 3A:
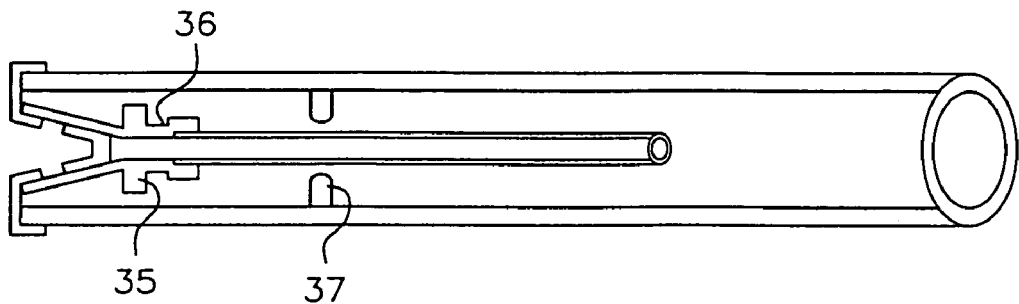
Figure 3B:
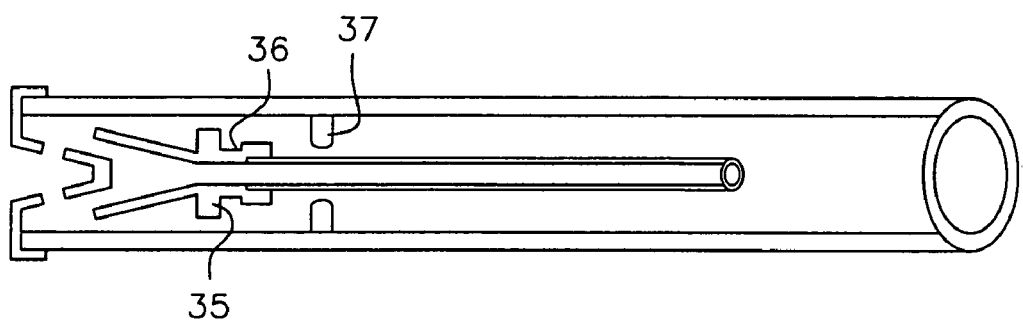
Figure 3C:
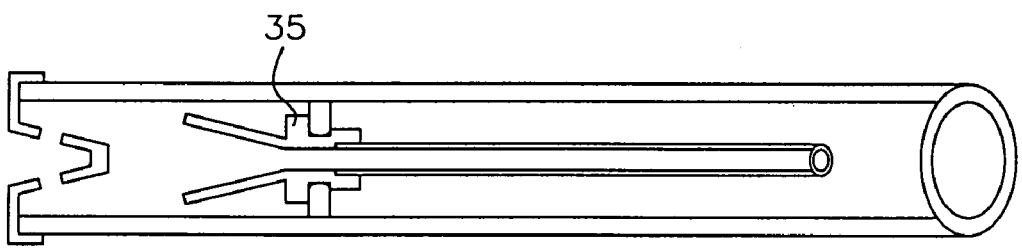
Figure 3D:
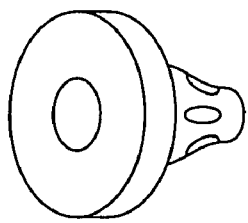
Figure 3E:
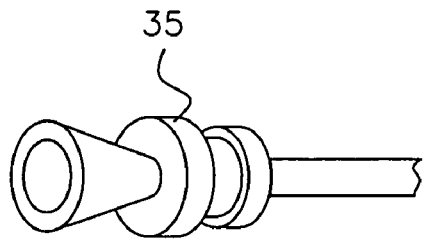
Figure 5A:
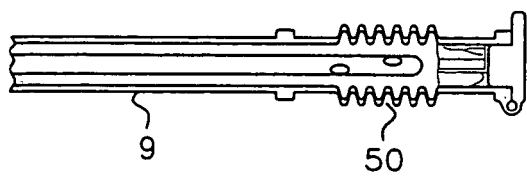
Figure 5B:
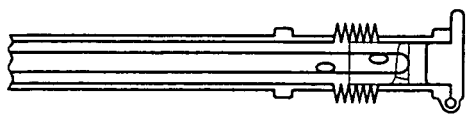
Figure 5C:
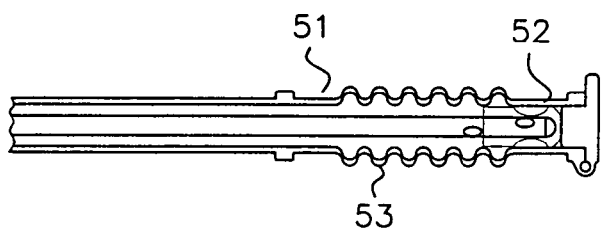
Figure 5D:
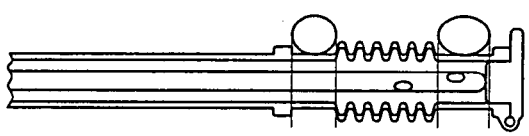
Figure 5E:
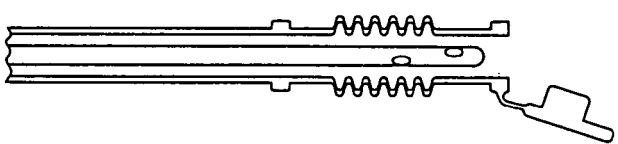
Figure 5F:
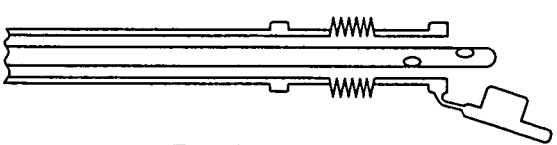
Figure 5G:
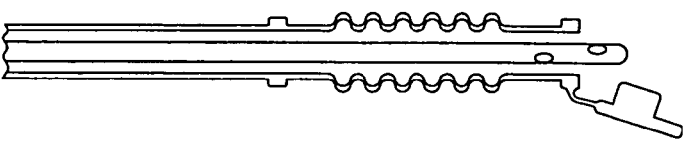

FIG. 3c shows a situation wherein the ring shaped member engages the groove. Likewise the embodiment of FIG. 2, the proximal ends of both the catheter and the package have been left out, In order to focus only on the differences between the embodiment of FIG. 2 and FIG. 3.

FIG. 4 shows an embodiment of the invention where the plug 45 comprises is provided with resilient vanes 46 provided with a diameter so that they over a first section 47 of the hose may contact the inner surface, when the plug is positioned within this section of the hose. However, the hose is provided with two different radial sizes. Accordingly, since the radial size of a second section 48 of the hose is larger than the radial size of the first section of the hose, the vanes 46 can not contact the inner surface of the hose, when the plug is positioned within the second section.

FIG. 5 shows an embodiment of the invention wherein the hose 9 is provided with a variable length. The variable length is provided via a concertina folded wall part 50 of the hose. The hose further forms two gripping zones 51,52 allowing the user to firmly grip the hose and shorten the length thereof, see e.g. FIG. 5b. As shown in the FIGS. 5a, 5b, 5c, 5d, 5e, 5f and 5g, the variable length allows the user to push the proximal catheter end out of the package by shortening the hose length, gripping the catheter through the hose wall, extending the hose length while the catheter is being gripped, releasing the grip and again shortening the length, vice versa. Accordingly, the hose wall 53 may preferably be made from a flexible material allowing the wall to be squeezed into contact with the catheter by finger pressure.

FIG. 6 shows an embodiment of the invention, wherein a compartment 60 is closed in a first end 61, whereas in a second opposite end 62 it is detachably connected with the hose member 63. The compartment is provided with two gripping zones 64,65 enabling the user to firmly grip the compartment. Moreover, the compartment is provided with a concertina folded wall section 66 enabling the user to reduce the length of the compartment, in order to push the proximal end of the catheter 67 out of the proximal end of the package. The closure 69 for closing the first end, is provided so that the package may be closed after the catheterisation. This will allow the user to store the used catheter assembly without any risk of contamination of the surroundings. However, as previously described, the first end 61 may also be closed by a tear-off compartment end, e.g. in the form of a thin foil glued to the end of the compartment.

Figure 6A:
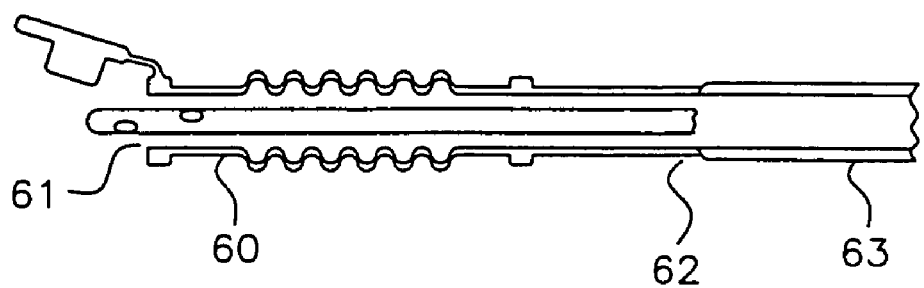
Figure 6B:
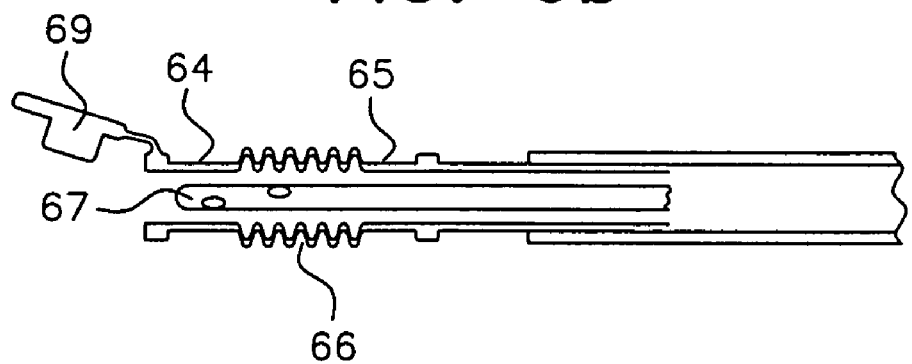
Figure 6C:
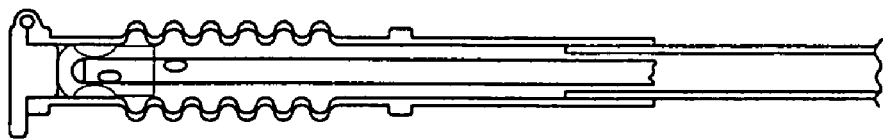

The compartment may be detachably connected to the hose over a tear-off line, see FIG. 6a or alternatively, the compartment may be connected to the hose member telescopically, by inserting one of either the hose or the compartment into the other one of the hose or the compartment, see FIGS. 6b, 6c.

Figure 7A:
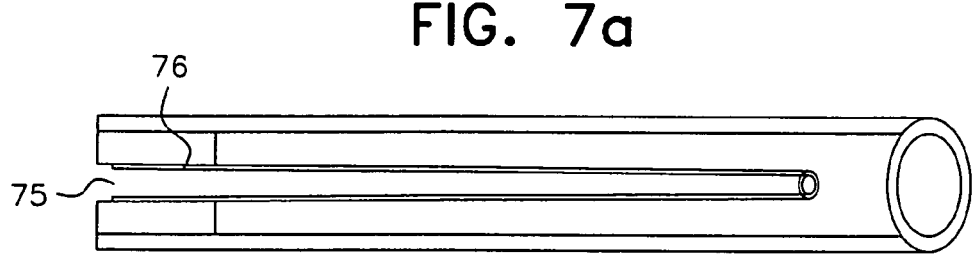
Figure 7B:
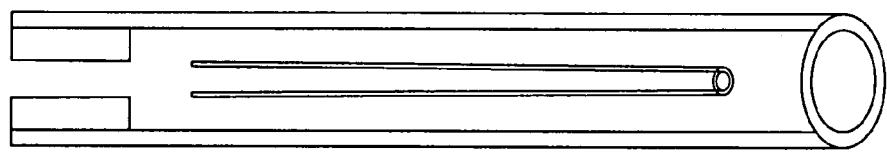
Figure 7C:
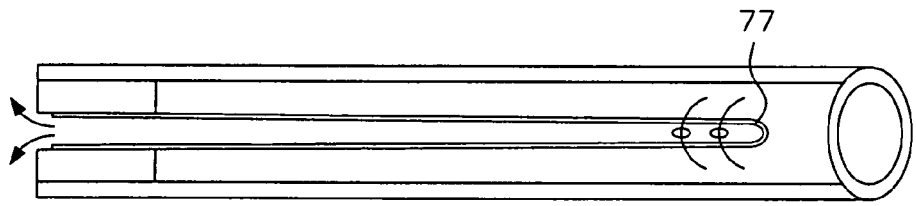

FIG. 7 shows a simple embodiment of the invention wherein the package, in its distal end is provided with an opening 75. The opening may be closed by the distal end 76 of the catheter itself, whereby the distal end of the package is automatically opened upon removal of the catheter from the catheter package. As indicated, a liquid substance comprised in the package, e.g. a liquid swelling medium for treatment of a hydrophilic catheter, is allowed to drain out of the package through the holes 77 provided in the proximal end of the catheter. The proximal end of the catheter and package is, for simplification of the drawing, left of the FIGS. 7a and 7b. In FIG. 7c, the proximal end of the package is left out. However, the proximal end of the package may be closed e.g. by a closure of any kind.

Figure 8A:
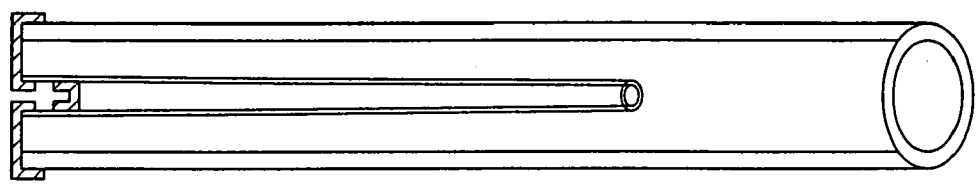
Figure 8B:
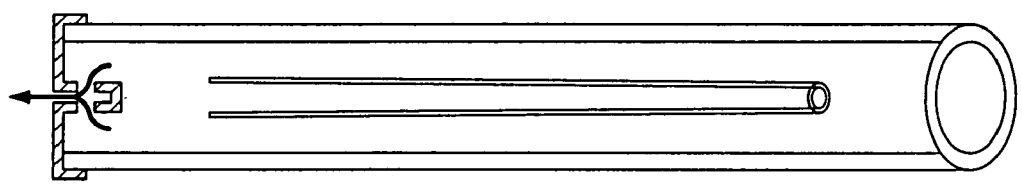
Figure 8C:
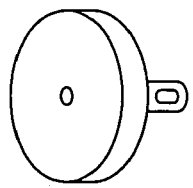

FIG. 8 shows an embodiment of the invention, wherein the distal end of the package is closed by a detachable closure 80. The closure is provided with an outlet 81 for draining liquid substances out of the package. In a first position of the catheter in relation to the package and the closure, see FIG. 8a, the outlet is closed by the distal end of the catheter. When the catheter is removed from the package, the outlet is opened, whereby liquid substances is drained out of the package.

Figure 9:
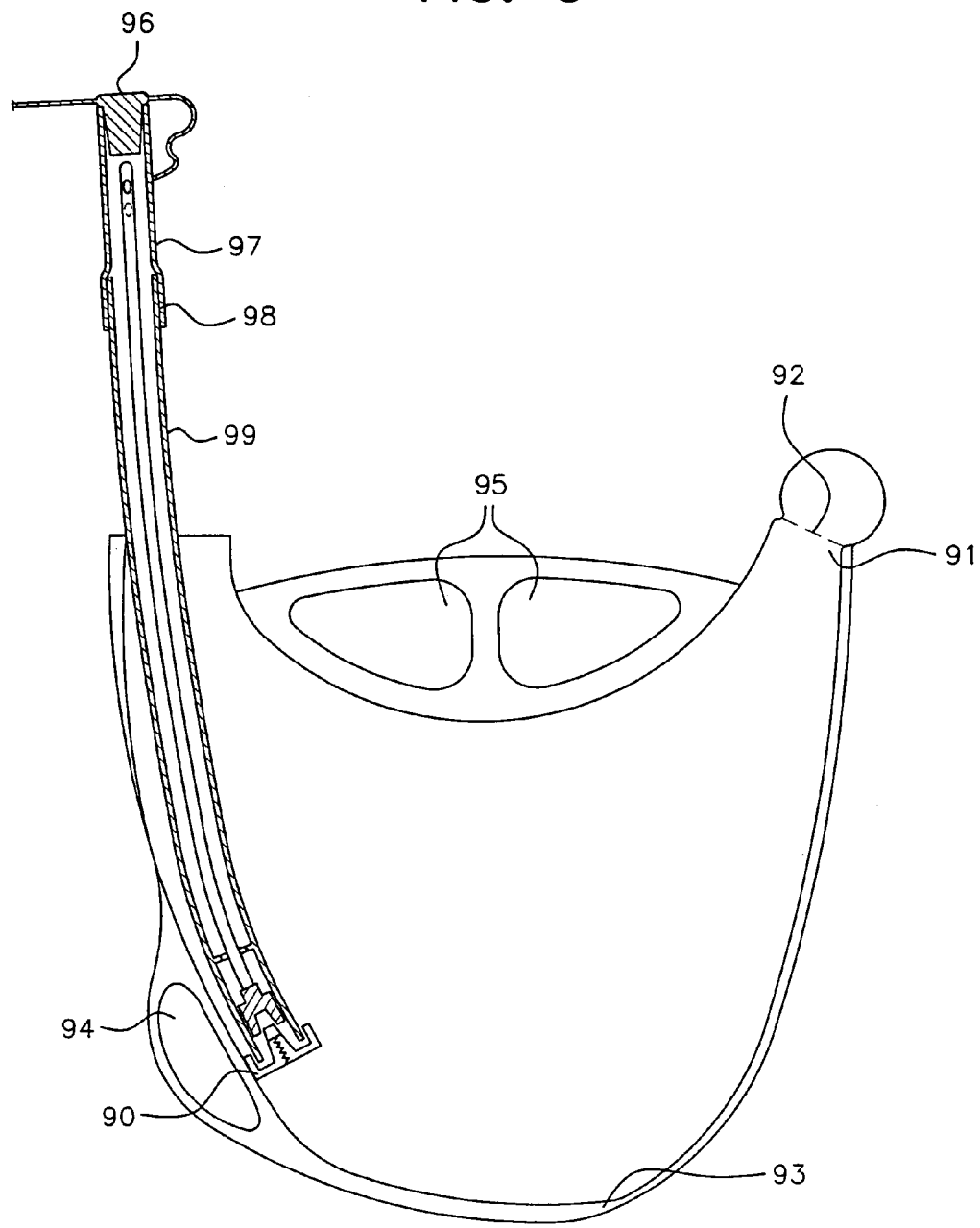
Figure 10:
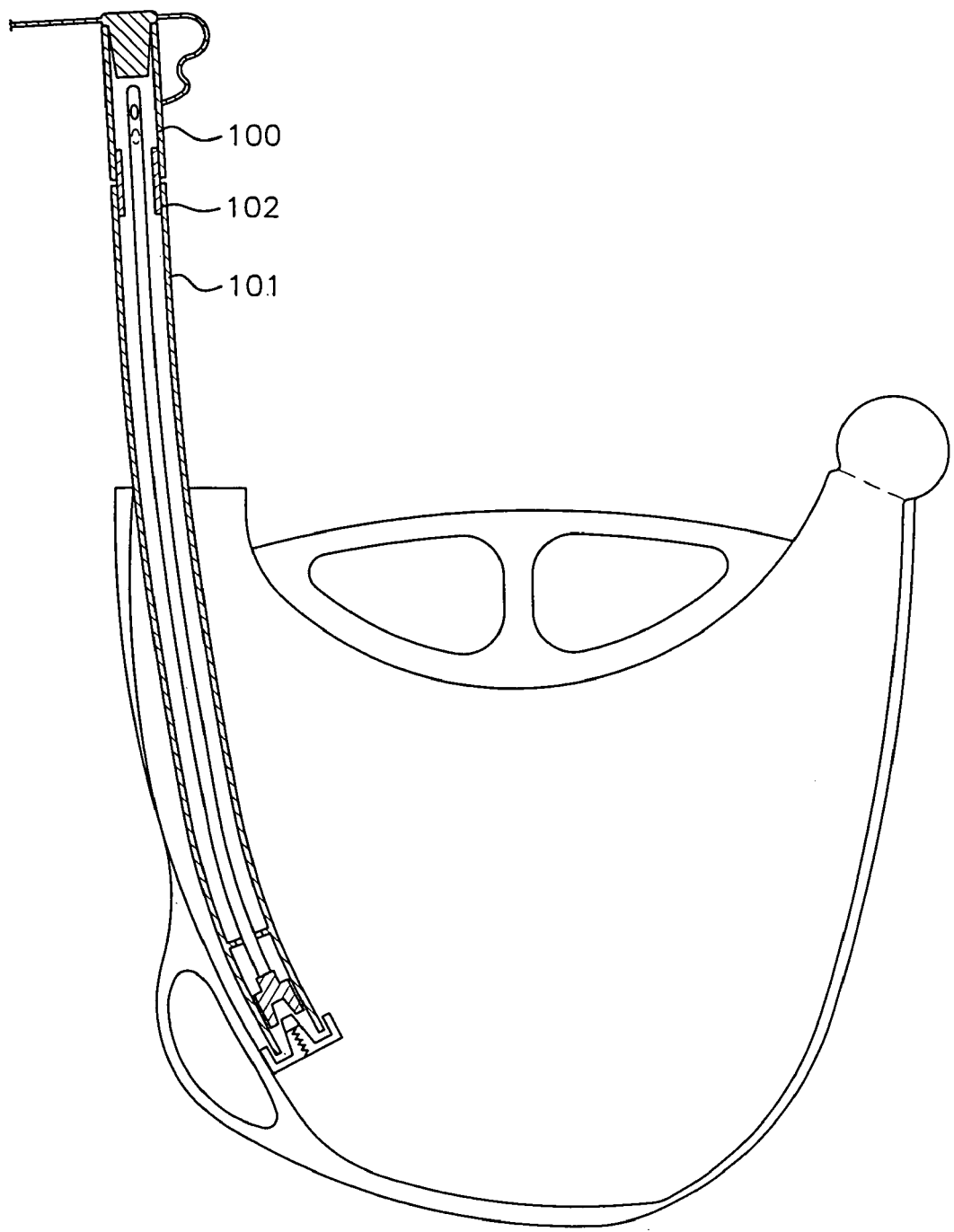
Figure 11:
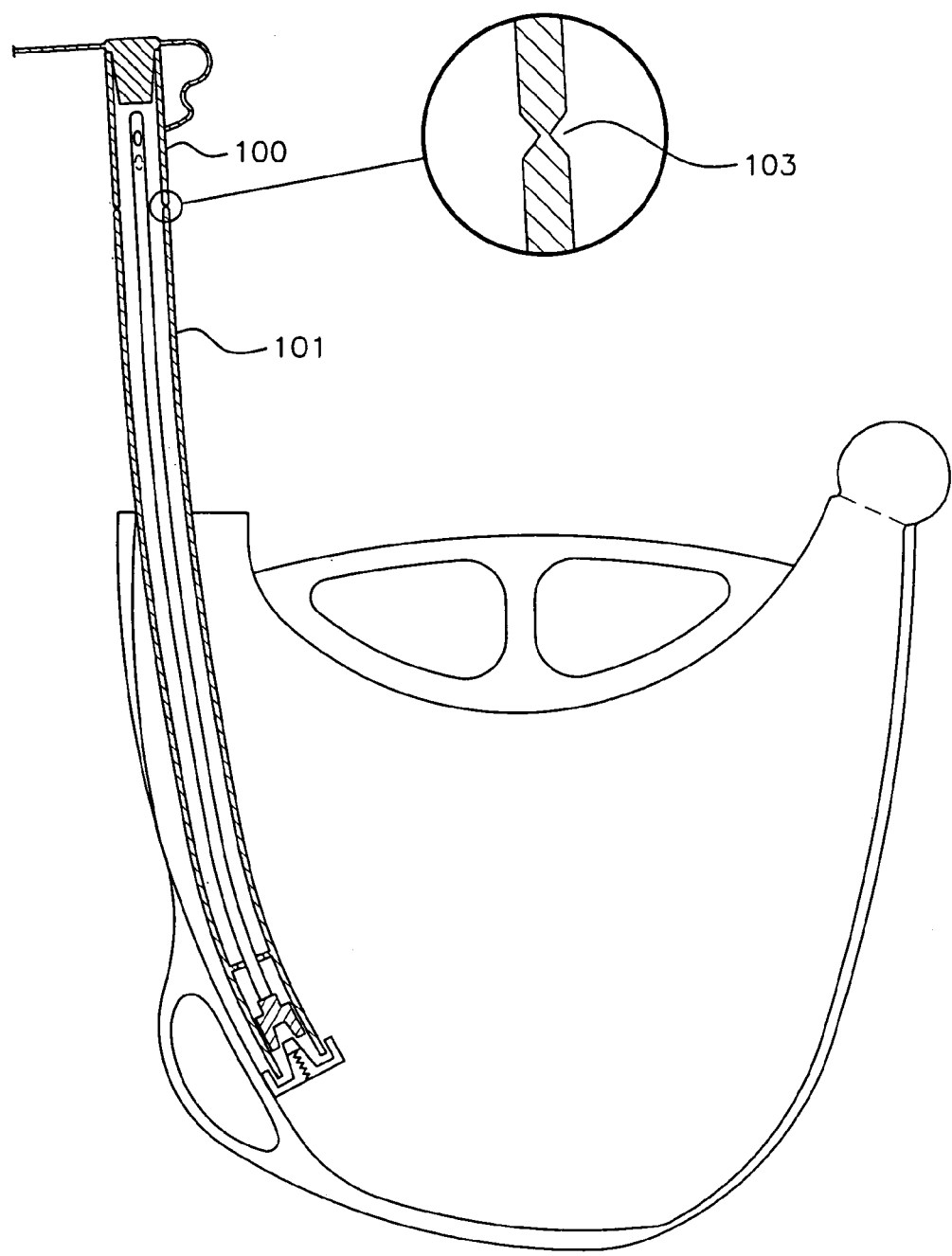

FIGS. 9–11 shows different embodiments of the invention wherein the hose member is connected to a reservoir for collection of liquid substances, e.g. for collection of urine and/or a saline solution having been used for establishing a low friction surface character of the catheter prior to use.

Referring to FIG. 9, the valve 90 may preferably be provided as a one-way closure, so as to ensure that liquids drained into the reservoir does not flow back through the hose member and/or through the catheter. The reservoir is provided with a draining spout or valve 91 for draining the liquid substances out of the reservoir. As an example, the draining valve may be opened by tearing off a top part of the valve. For this purpose the reservoir may preferably be provided with a weakening line 92. The reservoir may preferably be formed as a bag with a substantially flat bottom part 93. Thereby it will be possible for the user to leave the reservoir on a flat surface, e.g. on the floor, while the catheter is inserted into the urethra and while urine is drained into the reservoir. Instructions relating to the opening of the draining valve may preferably be printed on the reservoir. The handles 94, 95 give the user a better grip, e.g. when emptying the reservoir. For this purpose, it will be specifically appropriate to use both handles in combination, so that the reservoir is lifted in the top handles 95, while the rear handle 94 is used to rotate the reservoir. In this respect, it should be kept in mind that the user would typically be at least partly motorically disabled. The assembly further comprises a closure 96 for opening and closing the assembly, respectively. FIG. 9 shows an embodiment of the combined assembly and reservoir, wherein a compartment 97, in the joint 98 is telescopically joined to the hose 99.

FIG. 10 shows an embodiment of the assembly of FIG. 9, wherein a compartment 100 is attached to the hose member 101 by means of a coupling 102.

FIG. 11 shows an embodiment of the assembly of FIG. 10, wherein the compartment 100 is attached to the hose member 101 by means of a weakened tear-line 103.

It should be understood that the shown embodiments of the assembly wherein the catheter assembly is connected with a reservoir, may be used also in connection with indwelling catheters or in connection with any other kind of catheters. Likewise, the reservoir or bags may be used e.g. as a leg-bag, attached to the leg via leg-straps.

Figure 12:
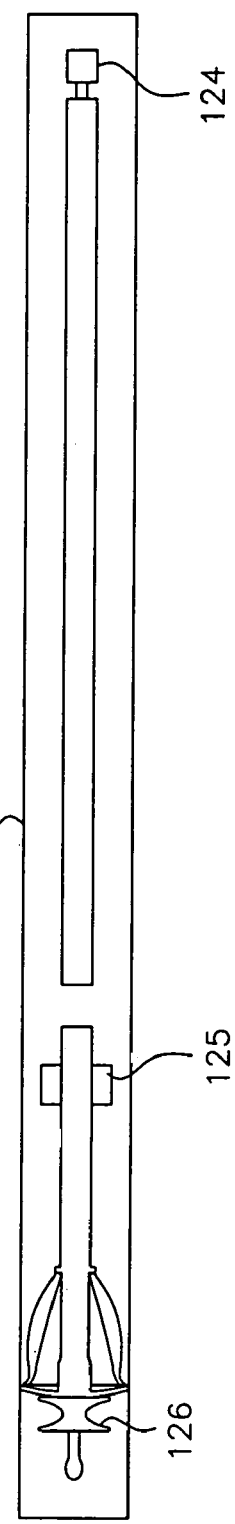
FIG. 12 shows a catheter assembly according to the present invention.

Referring to FIG. 12, an example of an advanced and particularly useful catheter assembly comprises a catheter 121 and a catheter package with a hose 122, an applicator 123, an opening 124 provided in the distal end of the package, a diamond 125 for adhesively bonding a bag to the hose and a closure 126. The applicator, the hose, the diamond and the closure is described further in the following Figs. As indicated in FIG. 12, the assembly may be enveloped in an outer package 127. By means of the outer package, all parts may be conveniently sterilised and the user can easily determine if the package has been opened, i.e. if the package is possibly contaminated.

Figure 13:
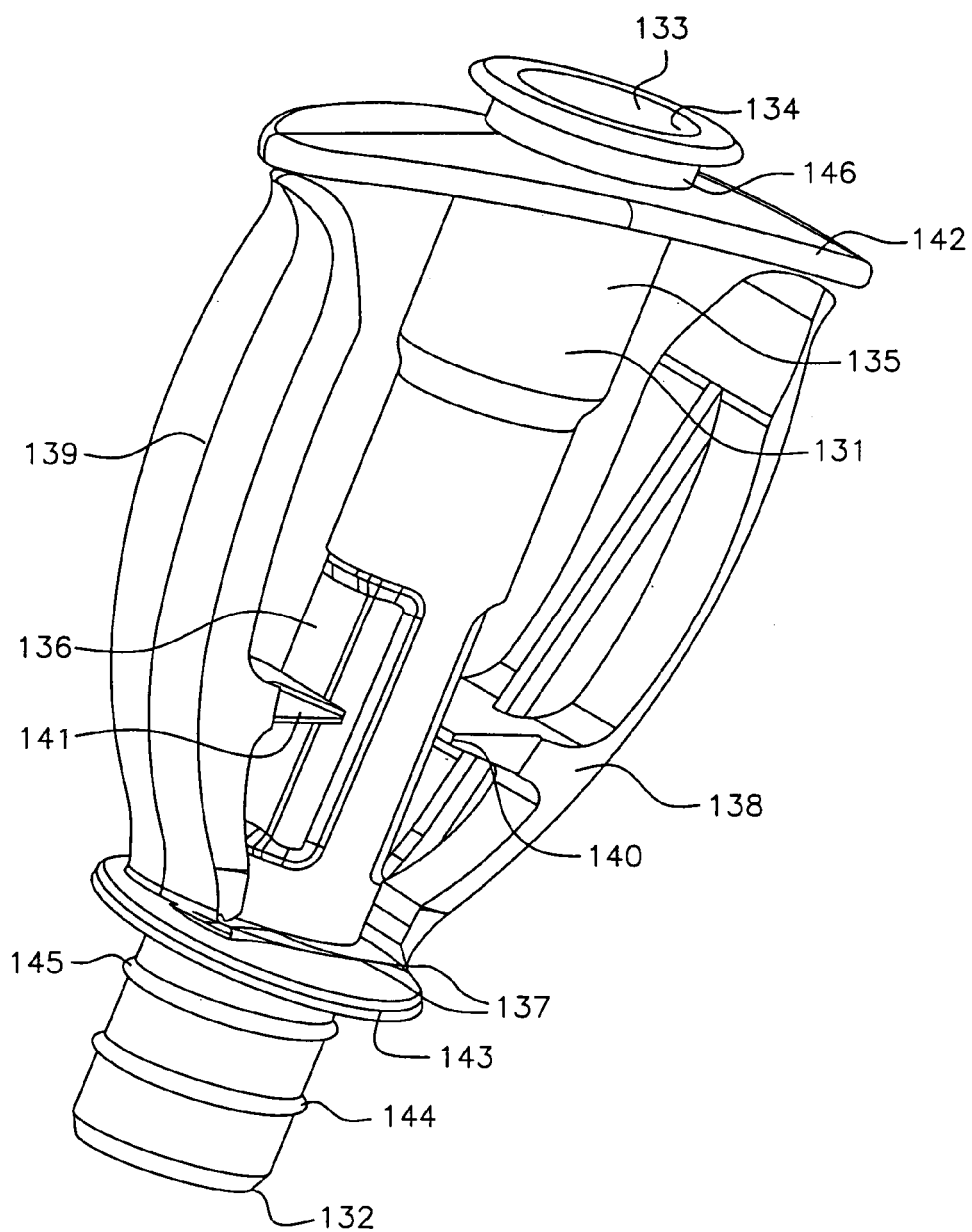
FIG. 13 shows a perspective view of an applicator for a medical utensil.
Figure 14:
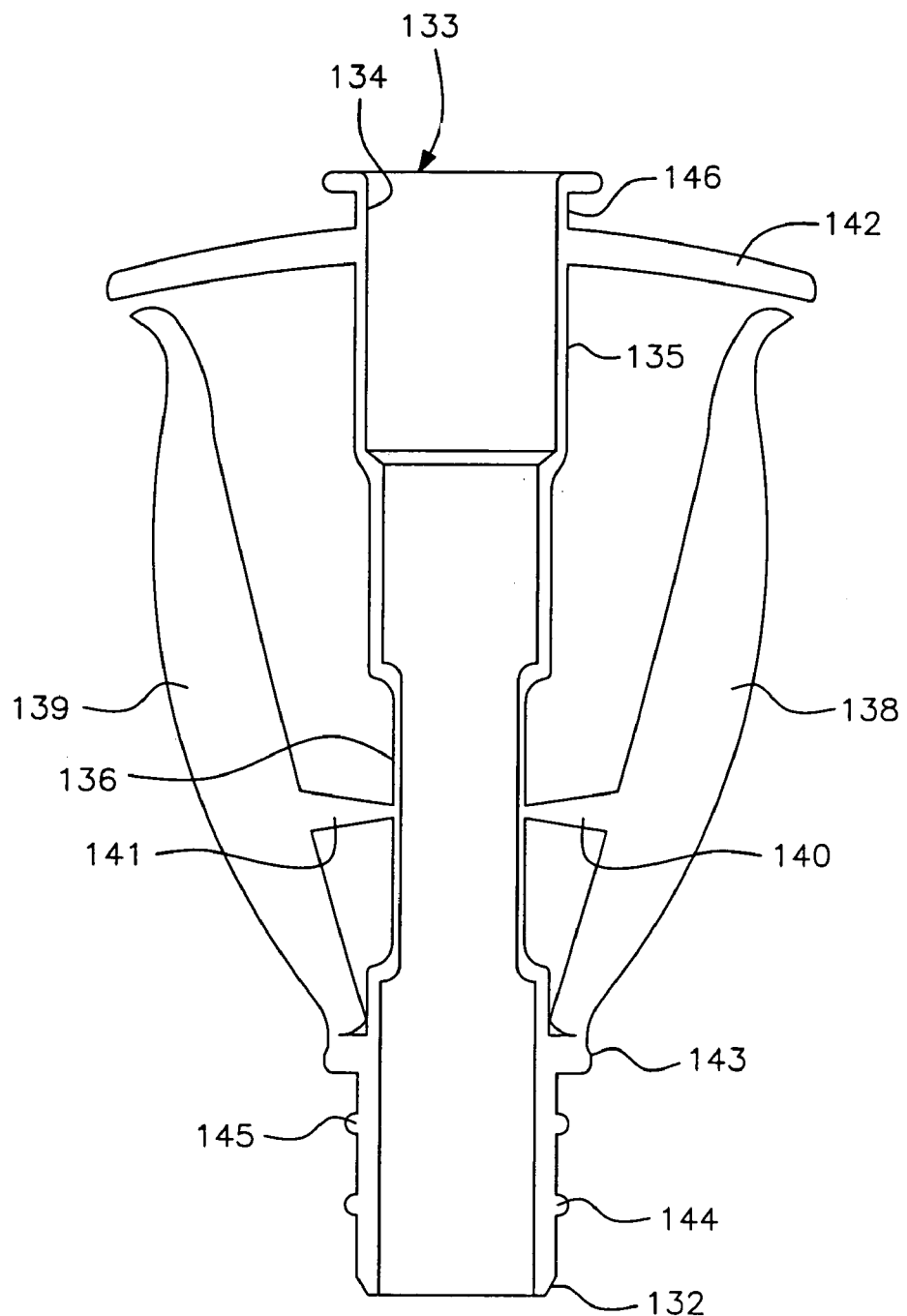
FIG. 14 shows a side view of the applicator shown in FIG. 13.
Figure 15:
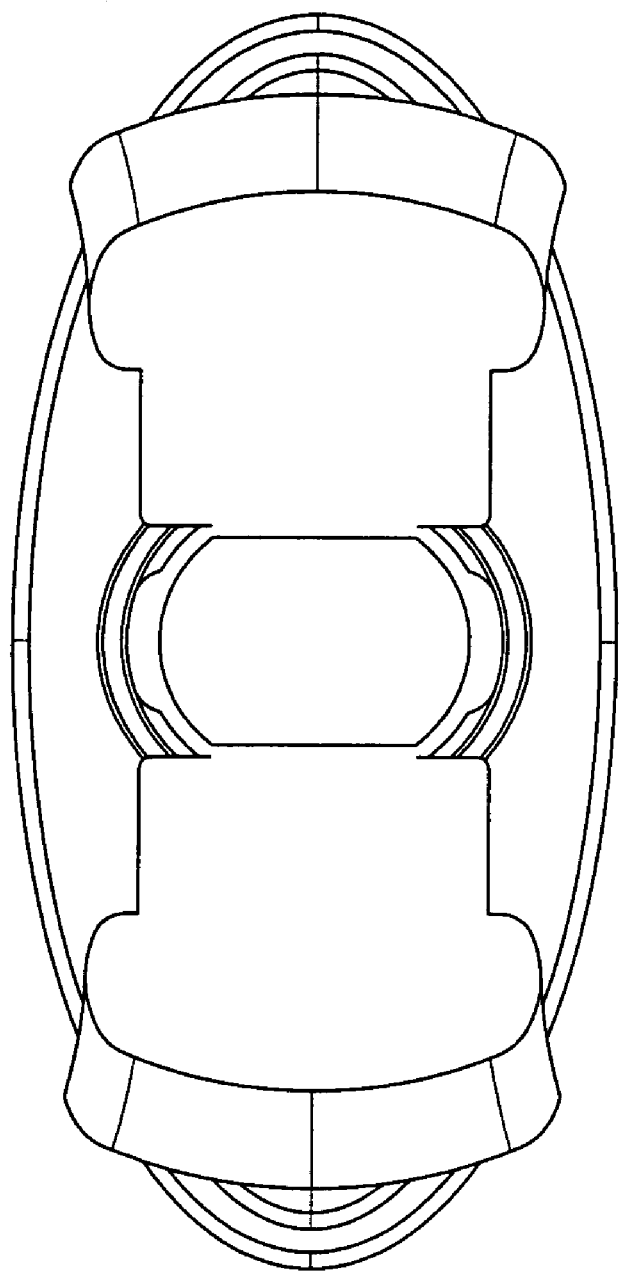
FIG. 15 shows a cross sectional along line A—A in FIG. 13.

FIGS. 13, 14 and 15 show an applicator for a medical utensil such as a catheter. The applicator is formed with a tubular compartment 131 with a first open end 132 and a second open end 133. The compartment extends between the open ends so that the applicator can be arranged on an oblong utensil. The compartment is formed with a wall having an inner surface 134 and an outer surface 135. The wall has at least one flexible zone 136 so that at least that part of the wall can be squeezed into engagement with the catheter upon a pressure applied to the outer surface of the wall. The applicator further comprises clamping means arranged to apply a pressure to the outer surface of the wall.

As shown, the tubular compartment 131 of the applicator may form a substantially linear passage between the open ends 132, 133. The clamping means comprises first and second handle members 138, 139. The handle members are joined to the applicator in first and second pivot points 137 allowing the handle member to be biased against the outer surface of the compartment wall. The handle members are arranged so that they are biased against opposite sides of the outer surface of the compartment. The handle members thus works as gripping members for gripping the catheter arranged therein between. The handle members are provided with a jaw-portion 140, 141. The jaw-portions extend perpendicularly from the handle members towards the flexible zones of the compartment. As best shown in FIG. 14, the jaw-portion may connect the handle member to the surface of the compartment wall. As an example and as indicated, the handle member, the jaw-portion and the compartment wall may be moulded in one single piece. The applicator further comprises an upper and a lower flange 142, 143 extending radially from points in the vicinity of the open ends 132, 133. The flanges have oval shapes and extend in mutual different radial directions from the tubular compartment—the upper flange 142 is rotated in the order of 90 degrees around the centre axis of the tubular compartment with respect to the lower flange 143. The applicator is provided with end parts 132, 133 which supports attachment of a closure to one end of the applicator and a hose for the package of the utensil to the other end of the applicator. The lower end part 132 is provided with one or more circumferentially extending protrusions 144, 145. This end part is adapted to be inserted into a hose like package member. The protrusions are adapted to engage the inner surface of such a hose for the provision of a sealing engagement therewith.

The upper end 133 of the compartment is provided with a circumferentially extending groove 146. The groove is provided for holding a fastening strip for a closure. A fastening strip is shown in FIG. 18 and a closure is shown in FIG. 16.

The closure disclosed in the FIGS. 16 and 17 may advantageously be used for closing a package for any kind of medical utensil, e.g. an oblong utensil such as a urinary catheter. The closure is provided with a sealing flange 161 having a number of radially outwardly extending protrusions 162, 163 adapted to engage the inner surface of a hose or applicator of a package. The closure is provided with a cavity 164 with a first open end 165. The cavity is provided with a radial size allowing the medical utensil, or at least an end-part thereof to project out of the package and into the closure. The depth of the cavity may advantageously be provided so that an appropriately large part of the utensil may extend into the closure, e.g. a length in the range of 1–5 cm. such as in the size of 2,5 cm. When the closure is removed from the package, the utensil, e.g. a catheter is easily accessible, since the one end of the utensil extends out of the open package. In order to allow more easily handling and removal of the closure from the package, the closure is provided with various gripping flanges 166, 167, 168. The upper and lower flange 166, 167 extends radially outwardly from the closure part, whereas the handling tab 168 extends in the "pull off" direction, parallel to the axial direction of the sealing flange and the cavity.

FIG. 18 shows a fastening strap with two ring-shaped members 181, 182 connected by a strap part 183. One of the ring-shaped members may be attached around the sealing flange of the closure and the other one may be attached around the hose of the package or around the applicator, thus ensuring that the closure is not lost.

FIG. 19 shows a view of a second valve member in the form of a combined valve member and a radially outwardly extending protrusion. The second valve member is adapted to be attached to a distal end of a catheter. The catheter member is on the outer surface provided with a sliding seal 191 (a piston seal) and a locking ring 192. The inner surface, which is best seen in FIG. 20, is provided with a second sealing flange 193 and a fourth sealing flange 194. FIG. 20 shows a first valve member to be provided in an opening of the package. The first valve member co-operates with the second valve member as described below. The first valve member comprises a first sealing flange 211 and a third sealing flange 212. Between the first and third sealing flanges, the first valve comprises one or more outlet openings 213 providing a passage between the inner lumen of the package and the surroundings. The second and fourth sealing flanges are adapted to engage with the corresponding first and third sealing flanges of a first valve member provided in an opening of the package. FIG. 21 shows a first valve member of the package. The first valve member is adapted to engage the corresponding second valve member of the catheter, cf. FIG. 19. Through the sealing engagement between the first sealing flange 211 of the first valve member, c.f. FIG. 21, and the second sealing flange 192 of the second valve member, a passage between the package or hose and the surroundings may be sealed. Through the sealing engagement between the third sealing flange 212 of the first valve member, c.f. FIG. 21, and the fourth sealing flange 193 of the second valve member, a passage between the conduit of the catheter and the surroundings may be sealed. When the catheter is removed from the package, or in fact already when a first part of the catheter is removed from the package, the second valve member is removed from the first valve member. Accordingly, the sealing engagement between the sealing flanges is removed and liquid substances both from the package and from the conduit of the catheter may flow out through the hole. The inner sealing flange 195 of the second valve member, c.f. FIG. 20, is provided for attaching the second valve member to a catheter, e.g. by adhesively bonding the valve to the outer surface of the distal catheter end. The catheter could also be moulded in one piece with an integrated valve part with features similar to the features of the valve of FIG. 20. The stepped configuration 214 of the first valve member, c.f. FIG. 21 is provided to support sealing engagement between the outer surface of the stepped part of the valve member and an inner surface of a hose of a catheter package. The first valve member may be adhesively bonded to the hose or the hose may be moulded in one piece with an integrated valve part with the features similar to the features of the valve of FIG. 21.

FIG. 23 shows a part of a hose for a package for a medical utensil. The hose is provided with a diamond 231 allowing the hose to be adhesively bonded to a bag, e.g. between two sheets of a foil material constituting the bag. The inner surface of the hose further comprises an inwardly extending flange or grove 232 adapted to receive a locking protrusion of the catheter. The flange or grove is provided in order to allow the catheter to be locked to a certain position inside the hose, i.e. to avoid that the catheter slides back into the package during the insertion or catheterisation. As an alternative, the locking arrangement may be formed as a radially outwardly extending flange or protrusion arranged on the inner surface of the hose for engagement with a radially inwardly extending depression or grove of the catheter. The sealing flange 233 is provided, e.g. for inserting one end of a catheter applicator into the hose.

Referring to FIG. 24, an applicator according to a preferred embodiment of the invention has a tubular compartment 241 with a lumen 242 extending axially in the direction visualised by the line 243 from a first end portion 244 to a second end portion 245. The applicator has a notch 246 circumferentially encircling the outer surface of the compartment. The applicator is further provided with outwardly extending handling means 247, 248 which are arranged in each of the two end portions.

The lumen 242 is more clearly shown in the cross-sectional view of the applicator of FIG. 25. The clearance 248 of the lumen narrows down towards the intermediate portion of the applicator. FIG. 26 shows a catheter extending through the applicator. As shown, the clearance 8 should be provided in a size allowing the catheter to slide in the axial direction—along the line 243—when the applicator is not kinked.

FIG. 27 shows a cross-sectional view of a kinked applicator and a catheter. The inner surface 271 of the applicator engages the outer surface 272 of the catheter whereby the frictional resistance against axial sliding of the catheter within the applicator is improved. The applicator shown in FIG. 27 provides a relatively narrow fit between the applicator and the catheter. It is to be understood though that an applicator showing a much wider clearance in similar way provides resistance against axial sliding as the kinked applicator will likewise engage with the catheter.

As shown in FIG. 28, inwardly extending gripping means 281 may be adapted to engage the outer surface of the catheter more firmly.

As shown in FIGS. 29a–29g, (FIGS. 29b–29g picturing the encircled segments of the applicator of FIG. 29a) the gripping means may have various shapes and sizes. As illustrated the gripping means may be constituted by a plurality of inwardly extending bulges.

FIG. 30 shows an applicator 301 which is attached to a connector part 302 of a catheter 304. The applicator and the connector part may be produced by moulding both parts in one piece, e.g. making the parts separable via a tear-off or break-off connection therein between, or the two parts may be glued together or assembled in any other way.

FIG. 31 shows an applicator 301 which is pressed onto the connector part 302 of a catheter 304.

As an example, the applicator may be made from a somewhat resilient material allowing one end of the applicator to be pressed onto the connector part. The connection 303 between the connector part and the applicator may preferably be provided as a liquid tight connection.

FIG. 32 shows a catheter assembly wherein the applicator 301 constitutes part of the package. One end of the applicator 321 is connected to the catheter connector 302 or alternatively, to a closure (not shown) and the other end of the applicator is connected to a sleeve-like package 322. The sleeve-like package 322 may contain a liquid medium or a gel for provision of a low friction surface character of the catheter.

FIG. 33 shows an applicator 301 attached to the plug part 331 of a catheter and both parts being packed in a sleeve-like envelope or package 332. The package is sealed along the sealing line 333, so that a liquid medium or gel is delimited to the lower part 334 of the package. This construction—plugging the end of the catheter—or an alternative construction (not shown) wherein a connector end is closed e.g. by a plug or a lid—ensures that contamination of the outer surface of the applicator with the liquid medium or gel is avoided.

FIG. 34 shows a catheter and an applicator packed in two individual lumens 341, 342 of the package. The package is made from two foils glued or welded together along the edge line 343 and along the separation line 344. Peeling the two foils from each other may open both the upper lumen 241 and the lower lumen 342. For that purpose, the package foils are provided with an over length defining the two peeling zones 345, 346.

Prior to insertion, the user may open the upper lumen 341 via the peeling zone 345. If the catheter is a hydrophilic catheter, the upper lumen may be used for adding a liquid swelling medium, e.g. water to the package before removal of the catheter. After the preparation which normally takes about 30 sec., the water may be drained from the package. The catheter may alternatively be packed in a swelled ready to use state. The next step is to separate the foils along the separation line 344, thus allowing the catheter to be guided through the applicator 301 and out of the opening in the peeling zone 346. By peeling a substantial part of the two foils from each other in the peeling zone 346, the user may remove the catheter from the package, only by touching the outside of the package and the applicator and thus perform a non-contaminating catheterisation.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An applicator for non-contaminating application of a medical utensil, said applicator comprising:
    a tubular compartment with a first open end, the compartment being adapted to receive at least a part of an utensil and being formed with a wall having an inner surface facing the utensil and an outer surface, the wall being provided with a flexible zone so as to allow the inner surface of the wall to be squeezed into engagement with the utensil upon a pressure applied to the outer surface of the wall;
    a clamping element including a first handle member joined to the applicator and being arranged to move between a first position in which said handle member applies pressure to the utensil arranged in the compartment by movement of said handle member toward said outer surface and a second at rest position in which the pressure is released, said handle member arranged to avoid engagement with other parts of the applicator so that movement between said first and second positions is unhindered; and
    a second handle member joined to the applicator and arranged to move between a first position in which said second handle member applies pressure to the utensil arranged in the compartment by movement of said handle member toward said outer surface and a second position in which the pressure is released, said second handle member being separated from the first handle member such that, during movement thereof and in both said first and second positions, said first and second handle members remain free of engagement with one another.

2. The applicator according to claim 1, wherein the compartment forms a substantially linear passage between the first open end and an opposite second open end, an inner diameter of said flexible zone being smaller than an inner diameter of adjacent portions of said wall on either side thereof.

3. The applicator according to claim 1, wherein said applicator is used to apply a urinary catheter having an insertable end into a urinary canal by bringing the wall of the compartment into contact with said insertable end, guiding a tip of the catheter into the urinary canal, releasing the grip, shifting the applicator to a new position along the catheter, gripping a next section of the catheter, and guiding the catheter further into the urinary canal until urine starts to drain through the catheter.

4. The applicator according to claim 1, wherein the second handle member is arranged in relation to the first handle member so as to bias against an opposite side of the outer surface of the compartment wall.

5. The applicator according to claim 1, wherein at least one of the first handle member or the second handle member further includes a jaw-portion that engages the flexible zone of the compartment wall when the first or the second handle member is biased against the outer surface of the compartment wall.

6. The applicator according to claim 5, wherein the jaw-portion extends substantially perpendicularly from the corresponding handle member.

7. The applicator according to claim 2, further comprising a first flange extending radially outwardly from the tubular compartment.

8. The applicator according to claim 7, wherein the first flange extends from a point in the vicinity of the first end of the compartment.

9. The applicator according to claim 8, further comprising a second flange extending radially from a point in the vicinity of the second end of the tubular compartment.

10. The applicator according to claim 9, wherein the first flange is oblong and extends primarily in a first direction perpendicular to the axial direction of the compartment.

11. The applicator according to claim 10, wherein the second flange is oblong and extends primarily in a second direction perpendicular to the axial direction of the compartment.

12. The applicator according to claim 11, wherein the second direction is offset 90 degrees around an axis parallel to the axial direction of the compartment.

13. The applicator according to claim 1, wherein the inner surface is provided with a protrusion extending radially inwardly for supporting a firm engagement between the inner surface and the compartment wall to be squeezed into engagement with the utensil upon a pressure applied to the outer surface of the wall.

14. The applicator according to claim 1, wherein the applicator is provided with a connecting flange for connecting the applicator to a package for a medical utensil.

15. The combination of a urinary catheter and an applicator for non-contaminating application of said catheter, said combination comprising:
    a urinary catheter having an end to be inserted into a patient's urinary canal for drainage of urine; and
    an applicator including a tubular compartment and a clamping element, said compartment having a first open end to receive at least a part of said catheter within said compartment and being formed with a wall having an inner surface facing said catheter and an outer surface, the wall having a flexible zone so as to allow the inner surface of the wall to be squeezed into engagement with the catheter within said compartment upon a pressure applied to the outer surface of the wall; and
    said clamping element including a handle with a first handle member and a second handle member, said first handle member being arranged to move between a first position in which said handle member applies pressure to said catheter within the compartment by movement of said handle member toward said outer surface and a second position in which the pressure is released, said handle member arranged to avoid engagement with other parts of the applicator so that movement between said first and second positions is unhindered;

said second handle member being arranged to move between a first position in which said second handle member applies pressure to said catheter within the compartment by movement of said handle member toward said outer surface and a second at rest position in which the pressure is released, said second handle member being separated from said first handle member such that, during movement thereof and in both said first and second positions, said first and second handle members remain free of engagement with one another; and said catheter being inserted into said patient urinary canal by bringing the wall of said compartment into contact with said catheter insertable end and gripping said catheter within said compartment while introducing a tip of said catheter into said urinary canal, releasing the grip and thereby allowing the handle to return to said second position, shifting the applicator to a new position along the catheter, returning said handle to said first position to grip a next section of said catheter, and guiding the catheter further into said urinary canal until urine starts to drain through said catheter.

* * * * *

UNITED STATES PATENT AND TRADEMARK OFFICE
CERTIFICATE OF CORRECTION

PATENT NO. : 7,094,220 B2  
APPLICATION NO. : 10/183984  
DATED : August 22, 2006  
INVENTOR(S) : Allan Tanghoj and Lars Bogelund Jensen It is certified that error appears in the above-identified patent and that said Letters Patent is hereby corrected as shown below:

In Col. 2, line 32, change "drained Into" to --drained into--;

In Col. 3, line 5, change "0,5 mm$^{2-50}$ mm$^2$" to --0,5 mm$^2$ – 50 mm$^2$--;

line 16, change "friction, character" to --friction character--;

In Col. 5, line 67, change "wail" to --wall--;

In Col. 10, line 34, change "In the" to --in the--;

In Col. 14, line 12, change "liquid, Is" to --liquid, is--;

line 66, change "Impermeable" to --impermeable--; and

In Col. 17, line 63, change "In order" to --in order--.

Signed and Sealed this

Nineteenth Day of August, 2008

JON W. DUDAS  
*Director of the United States Patent and Trademark Office*